(12) United States Patent
Liu et al.

(10) Patent No.: US 12,220,463 B2
(45) Date of Patent: Feb. 11, 2025

(54) QUATERNARY AMMONIUM CYCLODEXTRIN AND PREPARATION METHOD AND USES THEREOF, AND SILVER NANOPARTICLE-CYCLODEXTRIN COMPLEX AND PREPARATION METHOD AND USES THEREOF

(71) Applicant: Hubei University of Chinese Medicine, Wuhan (CN)

(72) Inventors: Junfeng Liu, Wuhan (CN); Junfeng Zan, Wuhan (CN); Ping Wang, Wuhan (CN); Guohua Zheng, Wuhan (CN); Laichun Luo, Wuhan (CN); Cong Chang, Wuhan (CN); Ke Yang, Wuhan (CN)

(73) Assignee: Hubei University of Chinese Medicine, Wuhan (CN)

( * ) Notice: Subject to any disclaimer, the term of this patent is extended or adjusted under 35 U.S.C. 154(b) by 0 days.

(21) Appl. No.: 18/493,090

(22) Filed: Oct. 24, 2023

(65) Prior Publication Data
US 2024/0156983 A1 May 16, 2024

(30) Foreign Application Priority Data
Oct. 26, 2022 (CN) .......................... 202211318142.3

(51) Int. Cl.
*A61K 47/69* (2017.01)
*A61P 31/04* (2006.01)

(52) U.S. Cl.
CPC ...... *A61K 47/6951* (2017.08); *A61K 47/6929* (2017.08); *A61P 31/04* (2018.01)

(58) Field of Classification Search
CPC . A61K 47/6951; A61K 47/6923; A61K 33/38
See application file for complete search history.

(56) References Cited

FOREIGN PATENT DOCUMENTS

CN 105461832 A 4/2016

OTHER PUBLICATIONS

Yang et al.; "Synthesis of cationic β-cyclodextrin functionalized silver nanoparticles and their drug-loading applications"; Mar. 6, 2023; RSC Adv., 13:7250-7256; DOI: 10.1039/d2ra08216k (Year: 2023).*

* cited by examiner

*Primary Examiner* — Timothy P Thomas
(74) *Attorney, Agent, or Firm* — Nitin Kaushik

(57) ABSTRACT

The present invention provides a cationic β-cyclodextrin and a preparation method and uses thereof, as well as a cationic β-cyclodextrin functionalized silver nanoparticles and a preparation method and uses thereof. The cationic β-cyclodextrin of the present invention is introduced with an amine group and quaternary ammonium groups, while retaining the special structure and properties of cyclodextrin itself. The amine group contained in the structure plays a role in reducing and complexing $Ag^+$ in the synthesis of AgNPs, and plays a certain role in stabilizing nanoparticles and forming a complex in combination with quaternary ammonium groups.

5 Claims, 19 Drawing Sheets

QUATERNARY AMMONIUM CYCLODEXTRIN AND PREPARATION METHOD AND USES THEREOF, AND SILVER NANOPARTICLE-CYCLODEXTRIN COMPLEX AND PREPARATION METHOD AND USES THEREOF

CROSS-REFERENCE TO RELATED APPLICATIONS

The application claims priority to Chinese patent application No. 2022113181423, filed on Oct. 26, 2022, the entire contents of which are incorporated herein by reference.

TECHNICAL FIELD

The present application relates to the technical field of cyclodextrin modification, in particular to a cationic β-cyclodextrin (C-β-CD) and a preparation method and uses thereof, as well as cationic β-cyclodextrin functionalized silver nanoparticles (C-β-CD/AgNPs) and a preparation method and uses thereof.

BACKGROUND

Cyclodextrins are a class of natural cyclic oligosaccharides generated from amylose by the action of cyclodextrin glycosyltransferase produced by *bacillus*. They typically contain 6 to 12 D-glucopyranose units. A cyclic conformation and the molecular arrangement of hydroxyl groups allow cyclodextrins to be present in an annular hollow truncated cone structure. Hydroxyl groups located in a cavity exterior confer cyclodextrins hydrophilicity, and a hydrophobic region is formed in a cavity interior under the shielding effect of C—H bonds, which allow CDs to form inclusion complexes with various hydrophobic guest molecules.

The most common cyclodextrins contain 6, 7 or 8 glucose units connected via α-1,4-glycosidic bonds, designated as α-cyclodextrin (α-CD), β-cyclodextrin (β-CD) and γ-cyclodextrin (γ-CD), respectively. Specifically, β-CD has been more widely studied and applied because it has a moderate cavity size, could be easily prepared, and is at a low price. However, practical applications of β-CD are limited by its relatively low water solubility to some degree. In order to overcome this problem, researchers have developed various β-cyclodextrin derivatives by modifying β-CD, such as hydroxypropyl-β-cyclodextrin (HP-β-CD) and sulfobutylether-β-cyclodextrin (SBE-β-CD). Cationization is an effective way to improve the water solubility of β-CD. Cationic β-cyclodextrin obtained after modification retains the cavity structure of cyclodextrin per se, and higher water solubility and positive charge further expand the application range of cyclodextrin.

Nanotechnology is an emerging research field in materials science, for studying the properties and applications of materials having a structural dimension in the range of 1 to 100 nm. Specifically, silver nanoparticles (AgNPs) have an extremely large specific surface area as their particle size is relatively small, and exhibit significantly different chemical and physical properties from macroscopic materials. They are widely used in medicine, environment, cosmetics, optoelectronics, catalysis, textiles, food and other fields. Especially in the biomedical field, antibacterial properties of AgNPs have been widely studied and applied.

Biological and chemical activities of AgNPs are related to a series of parameters, such as size, shape, monodispersity and stability, and these parameters predominantly depend on the environment in which AgNPs are synthesized. There are many types of AgNPs, and various methods for preparing AgNPs, such as chemical reduction, photolysis and ultrasonic microwave radiation. Chemical reduction of a transition metal precursor salt in the presence of a chemical stabilizer and a reducing agent is the most common method for preparing AgNPs, but chemical synthesis involves the use of agent materials that may be toxic and harmful to the environment, with potential environmental and health concerns. Therefore, the green synthesis of metal nanoparticles has become an important research direction in the field of materials. Some biocompatible agents, e.g., polymers and polysaccharides, have been used in the green synthesis of nanoparticles under environment-friendly conditions. As a class of natural cyclic oligosaccharide macromolecules, cyclodextrins containing numerous hydroxyl groups in the structure may be used as a reducing agent to reduce metal salts under alkaline conditions, and can be adsorbed on the surface of metal nanoparticles in the synthesis of metal particles, effectively stabilizing metal nanoparticles and preventing aggregation. In recent years, researchers have conducted in-depth research on cyclodextrins as a stabilizer and a reducing agent. So far, few studies have used cationic cyclodextrin modified with quaternary ammonium groups as a reducing agent and a stabilizer in the synthesis of cyclodextrin complexes of AgNPs.

SUMMARY

In this regard, the present application provides cationic β-cyclodextrin, and a preparation method and uses thereof, as well as a cationic β-cyclodextrin functionalized silver nanoparticles, and a preparation method and uses thereof; and modifies a cyclodextrin and uses the modified cyclodextrin as a reducing agent to synthesize a cyclodextrin complex of AgNPs.

In a first aspect, the present invention provides a cationic β-cyclodextrin which has a structural formula as represented below:

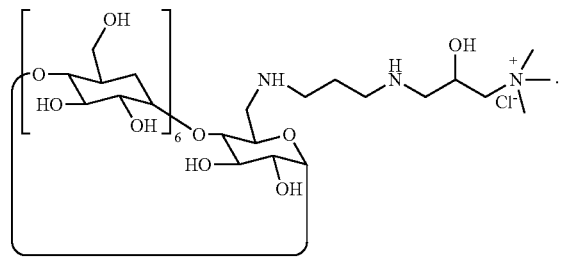

Preferably, a method for preparing the cationic β-cyclodextrin comprises following steps:
  dissolving β-cyclodextrin in an alkaline solution, and adding p-toluenesulfonyl chloride to the alkaline solution at 0-5° C., followed by stirring and reaction, to afford toluenesulfonyl-β-cyclodextrin (Ts-β-CD); and
  dissolving the toluenesulfonyl-β-cyclodextrin in 1,3-propanediamine and reacting at 70-90° C. to afford diaminopropane-β-cyclodextrin (DAP-β-CD); and
  dissolving 2,3-epoxypropyltrimethylammonium chloride in dimethyl sulfoxide, then adding the diaminopropane-β-cyclodextrin, and reacting at 70-90° C. to afford cationic β-cyclodextrin.

Preferably, as for the method of preparing cationic β-cyclodextrin, in the step of preparing toluenesulfonyl-β-cyclodextrin, a mass-volume ratio of the β-cyclodextrin, the p-toluenesulfonyl, and the alkaline solution is (45-55) g:(30-40) g:(450-550) mL;

the alkaline solution is a sodium hydroxide solution, wherein the sodium hydroxide solution has a concentration of 0.3-0.5 M.

Preferably, as for the method of preparing cationic β-cyclodextrin, in the step of preparing the diaminopropane-β-cyclodextrin, a mass-volume ratio of the toluenesulfonyl-β-cyclodextrin to the 1,3-propanediamine is (3-5) g:(15-25) mL.

Preferably, as for the method of preparing cationic β-cyclodextrin, in the step of dissolving 2,3-epoxypropyltrimethylammonium chloride in dimethyl sulfoxide and then adding diaminopropane-β-cyclodextrin, a mass-volume ratio of the 2,3-epoxypropyltrimethylammonium chloride, the diaminopropane-β-cyclodextrin, and the dimethyl sulfoxide is (0.4-0.8) g:(4-5) g:(5-15) mL.

In a second aspect, the present invention further provides use of the cationic β-cyclodextrin or cationic β-cyclodextrin prepared by the method as a drug carrier or a reducing agent in the preparation of metal nanoparticles.

Preferably, in the use the cationic β-cyclodextrin is used as a drug carrier to encapsulate thymol or cinnamaldehyde.

In a third aspect, the present invention also provides a method for preparing a cationic β-cyclodextrin functionalized silver nanoparticles, comprising:

adding the cationic β-cyclodextrin to water and adjusting a pH to 10-12, then adding a silver nitrate solution and reacting at 50-70° C. to afford the cationic β-cyclodextrin functionalized silver nanoparticles.

In a fourth aspect, the present invention also provides the cationic β-cyclodextrin functionalized silver nanoparticles prepared by the preparation method.

In a fifth aspect, the present invention also provides a use of the cationic β-cyclodextrin functionalized silver nanoparticles for inclusion of the thymol and as a bacteriostatic agent.

The cationic β-cyclodextrin and the preparation method and uses thereof, as well as the cationic β-cyclodextrin functionalized silver nanoparticles and the preparation method and uses thereof in the present invention have the following beneficial effects over the prior art:

1. The cationic β-cyclodextrin of the present invention is introduced with an amine group and quaternary ammonium groups, while retaining the special structure and properties of the cyclodextrin itself. The amine group contained in the structure plays a role in reducing and complexing $Ag^+$ in the synthesis of AgNPs, and plays a certain role in stabilizing nanoparticles in combination with quaternary ammonium groups;

2. The method for preparing cationic β-cyclodextrin of the present invention uses 1,3-propanediamine as a raw material, which is cheaper and easily available compared with ethylenediamine. Moreover, 1,3-propanediamine has a moderately extended carbon chain compared with ethylenediamine, and thus is beneficial to retaining the cyclodextrin function after subsequent grafting and complex formation. Specifically, FIG. 18 shows that C-β-CD/AgNPs retain the drug-loading function of cationic cyclodextrin;

3. The method for preparing a cationic β-cyclodextrin functionalized silver nanoparticles of the present invention uses cationic β-cyclodextrin (C-β-CD) as a reducing agent and a stabilizer to prepare spherical silver nanoparticles having a small particle size and good stability. UV-Vis results show that C-β-CD/AgNPs produce a typical plasmon absorption band of silver nanoparticles at 401 nm; TEM image shows that C-β-CD/AgNPs particles are present in the shape of a sphere and have a particle size of 3-13 nm; XRD results demonstrate the synthesis of face-centered cubic elemental silver; Zeta potential shows that the C-β-CD/AgNPs solution has high stability; FT-IR reveals the modification and reduction effect of the cationic β-cyclodextrin (C-β-CD) to AgNPs. The cationic β-cyclodextrin (C-β-CD) retains the special structure and properties of the cyclodextrin itself. The amine group contained in the structure plays a role in reducing and complexing $Ag^+$ in the synthesis of AgNPs, and plays a certain role in stabilizing nanoparticles in combination with quaternary ammonium groups;

4. The method of preparing a silver nanoparticle cyclodextrin complex of the present invention is characterized by mild reaction conditions, a fast reaction process, easy availability of raw materials and clear product characteristics. The cationic β-cyclodextrin prepared by the present invention can be used as a drug carrier and as a reducing agent for the preparation of metal nanoparticles. The cationic cyclodextrin-functionalized silver nanoparticles of the present invention have application potential in antibiosis, drug delivery and catalysis; and 5. The complex of silver nanoparticles and cationic β-cyclodextrin of the present invention can be used to encapsulate thymol, and as a bacteriostatic agent exhibits a stronger bactericidal effect than the simple substance silver nanoparticles.

BRIEF DESCRIPTION OF DRAWINGS

To illustrate the technical solutions in the examples of the present invention or in the prior art more clearly, the accompanying drawings required for describing the examples or the prior art are briefly described below. Apparently, the accompanying drawings in the following description show merely some examples of the present invention, and a person of ordinary skill in the art may still derive other drawings from these accompanying drawings without inventive efforts.

DETAILED DESCRIPTION OF THE EMBODIMENTS

Figure 1:
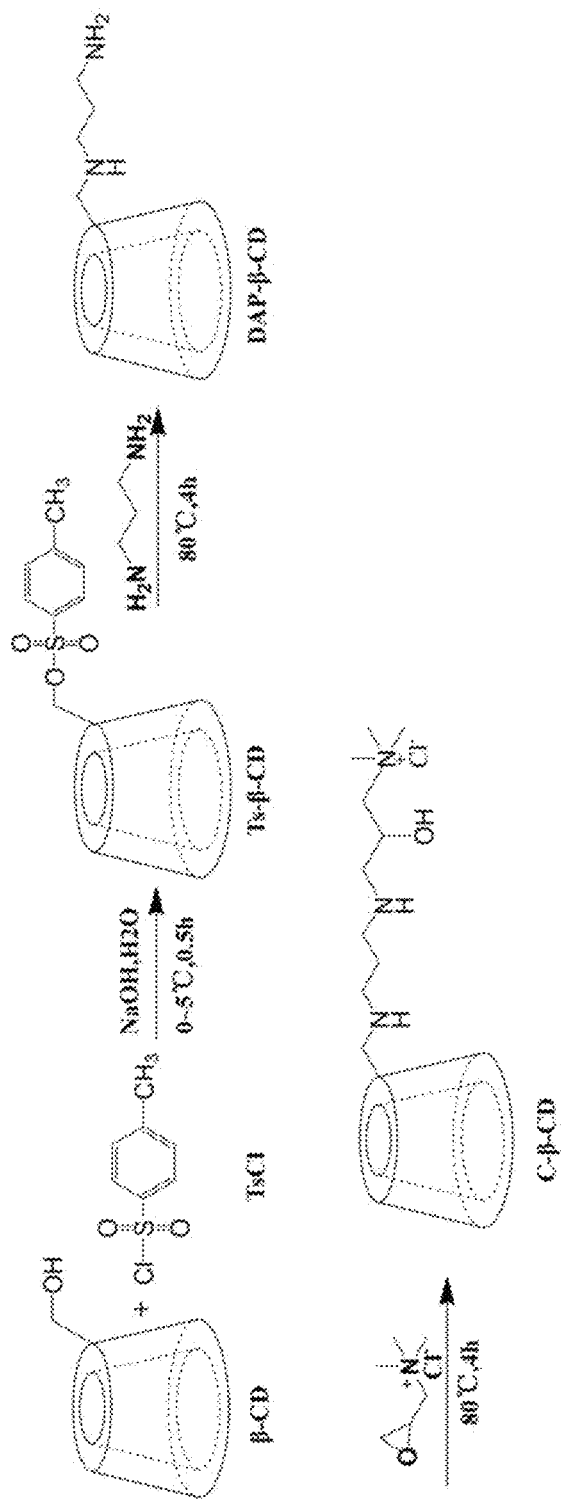
FIG. 1 is a process diagram illustrating a method for preparing cationic β-cyclodextrin of the present invention.

The technical solutions of the embodiments in the present invention are clearly and completely described below with reference to the embodiments. Apparently, the described embodiments are a part rather than all of the embodiments of the present invention. All other embodiments obtained by a person of ordinary skill in the art based on the embodiments of the present invention without inventive efforts shall fall within the protection scope of the present invention.

The present invention provides a cationic β-cyclodextrin, which has a structural formula as represented below:

It should be noted that the cationic β-cyclodextrin in the present application is in a structure that one —OH on β-cyclodextrin (β-CD) is substituted with Based on the same inventive concept, the embodiment of the present application further provides a method of preparing cationic β-cyclodextrin, comprising the following steps:

S1: dissolving β-cyclodextrin in an alkaline solution, and adding p-toluenesulfonyl chloride to the alkaline solution at 0-5° C., followed by stirring and reaction, to afford toluenesulfonyl-β-cyclodextrin; and S2: dissolving the toluenesulfonyl-β-cyclodextrin in 1,3-propanediamine and reacting at 70-90° C. to afford diaminopropane-β-cyclodextrin; and S3: dissolving 2,3-epoxypropyltrimethylammonium chloride in dimethyl sulfoxide, then adding the diaminopropane-β-cyclodextrin, and reacting at 70-90° C. to afford the cationic β-cyclodextrin.

The method for preparing cationic β-cyclodextrin in the present application comprises first synthesizing the precursor compound toluenesulfonyl-β-cyclodextrin (Ts-β-CD) under alkaline conditions; then performing a nucleophilic substitution reaction of toluenesulfonyl-β-cyclodextrin (Ts-β-CD) with 1,3-propanediamine to afford diaminopropane-β-cyclodextrin(DAP-β-CD), wherein the diaminopropane-β-cyclodextrin (DAP-β-CD) is in the following structural formula:

and performing an epoxide ring-opening reaction of 2,3-epoxypropyltrimethylammonium chloride (EPTAC) with a diaminopropane-β-cyclodextrin (DAP-β-CD), to prepare cationic β-cyclodextrin (C-β-CD).

Specifically in some embodiments, in the step of preparing toluenesulfonyl-β-cyclodextrin, a mass-volume ratio of the β-cyclodextrin, the p-toluenesulfonyl and the alkaline solution is (45-55) g:(30-40) g:(450-550) mL;

the alkaline solution is a sodium hydroxide solution, wherein the sodium hydroxide solution has a concentration of 0.3-0.5 M.

In some embodiments, in the step of preparing diaminopropane-β-cyclodextrin, a mass-volume ratio of the toluenesulfonyl-β-cyclodextrin to the 1,3-propanediamine is (3-5) g:(15-25) mL.

In some embodiments, in the steps of dissolving 2,3-epoxypropyltrimethylammonium chloride in dimethyl sulfoxide and then adding the diaminopropane-β-cyclodextrin, a mass-volume ratio of the 2,3-epoxypropyltrimethylammonium chloride, the diaminopropane-β-cyclodextrin, the dimethyl sulfoxide is (0.4-0.8) g:(4-5) g:(5-15) mL.

In some embodiments, step S1 specifically comprises: dissolving 45-55 g β-cyclodextrin in 450 to 550 mL of a 0.3 to 0.5 M sodium hydroxide solution (0 to 5° C.); adding 30-40 g p-toluenesulfonyl chloride (TsCl) to the sodium hydroxide solution in batches within 5 min and stirring for 30-40 min; after quickly removing unreacted TsCl via suction filtration, neutralizing the filtrate pH to 7-9 with 2-4 M HCl; stirring for 1-2 h; precipitating the resultant precipitate followed by suction filtration; washing the obtained white precipitate twice with ultrapure water and three times with acetone; and then drying under vacuum at 30-50° C. to afford toluenesulfonyl-β-cyclodextrin (Ts-β-CD).

In some embodiments, step S2 specifically comprises: dissolving 3-5 g toluenesulfonyl-β-cyclodextrin in 15-25 mL 1,3-propanediamine; reacting at 70-90° C. for 3-5 h; after free cooling to room temperature, pouring into ethanol and precipitating the resultant precipitate followed by suction filtration; washing the obtained white precipitate with ethanol, and then drying under vacuum at 30-50° C. to afford diaminopropane-β-cyclodextrin (DAP-β-CD).

In some embodiments, step S3 specifically comprises dissolving 0.4-0.8 g 2,3-epoxypropyltrimethylammonium chloride in 5-15 mL dimethyl sulfoxide (DMSO); then adding 4-5 g the diaminopropane-β-cyclodextrin (DAP-β-CD); reacting at 70-90° C. for 3-5 h; after free cooling to room temperature, pouring into ethanol and precipitating the resultant precipitate followed by suction filtration; washing the obtained white precipitate with ethanol and drying under vacuum at 30-50° C. to afford cationic β-cyclodextrin (C-β-CD).

Specifically, FIG. 1 shows the process route diagram illustrating a method for preparing cationic β-cyclodextrin of the present invention; wherein for convenience of presentation,

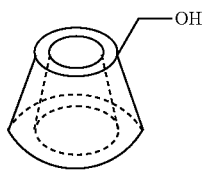

Based on the same inventive concept, the embodiment of the present application further uses the aforesaid cationic β-cyclodextrin as a drug carrier and a reducing agent in the preparation of a cationic β-cyclodextrin functionalized silver nanoparticles.

Specifically, the aforesaid cationic β-cyclodextrin as a drug carrier is used in the inclusion of the volatile bacteriostatic agent thymol or the volatile tyrosinase inhibitor cinnamaldehyde.

Based on the same inventive concept, the present invention also provides a method for preparing a cationic β-cyclodextrin functionalized silver nanoparticles, comprising:
    adding the cationic β-cyclodextrin to water and adjusting a pH to 10-12, then adding a silver nitrate solution and reacting at 50-70° C. to afford cationic cyclodextrin-functionalized silver nanoparticles.

Specifically, 3-7 mL a cationic β-cyclodextrin solution at a concentration of 0.01 to 0.02 M (which is obtained by adding cationic β-cyclodextrin to water) is added to 30 to 35 mL water, to which 2-3 mL a 0.1-0.2 M NaOH solution is added with stirring so that the pH is 10-12; and then 0.5-1 mL a 0.1-0.2 M silver nitrate solution is added and reacted with stirring at 60° C. for 1-2 h to afford a C-β-CD/AgNPs solution, in which a cationic β-cyclodextrin functionalized silver nanoparticles (C-β-CD/AgNPs) is comprised.

Figure 2:
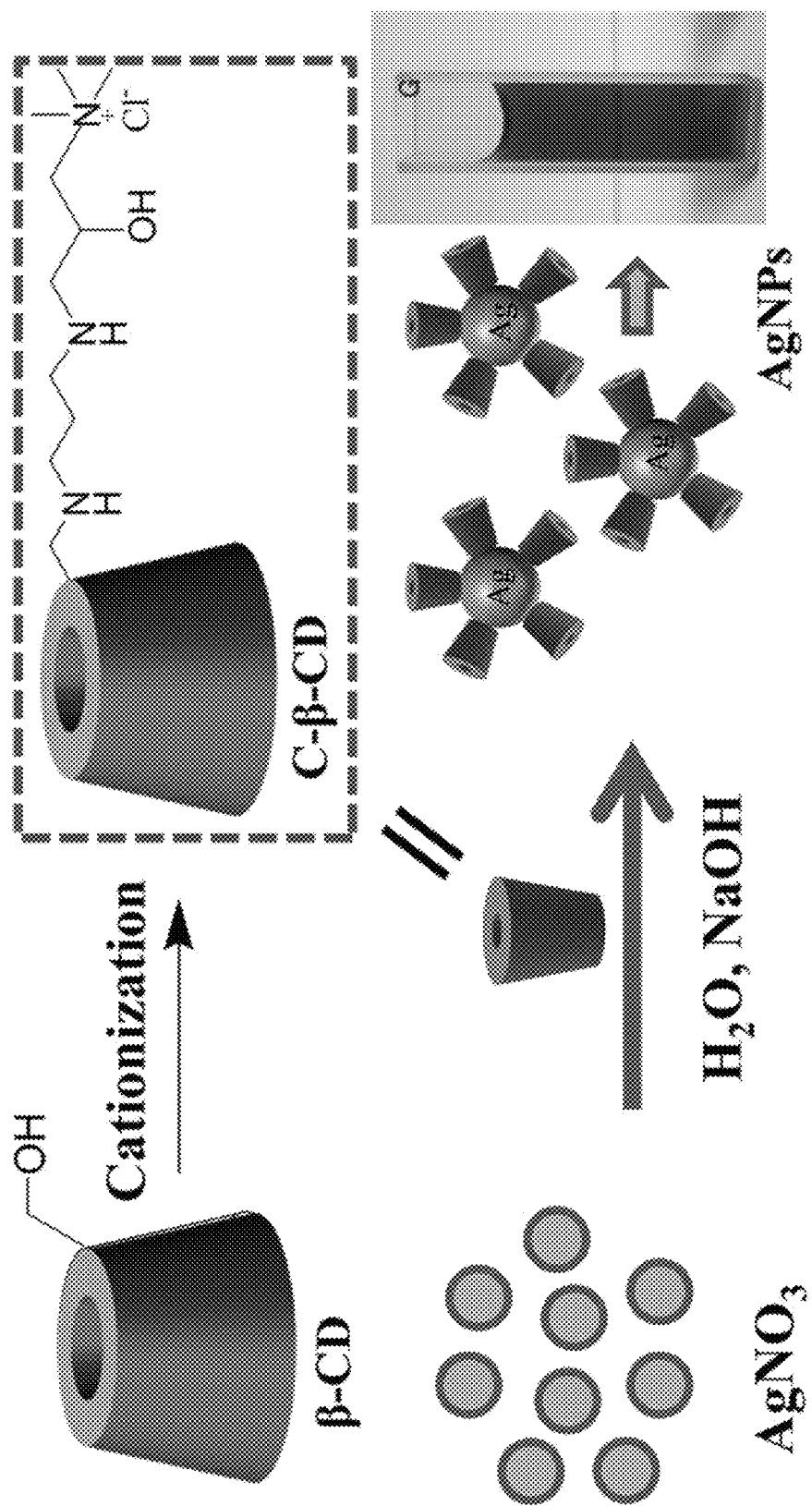
FIG. 2 is a process diagram illustrating a method for preparing silver nanoparticles of the present invention.

Specifically, FIG. 2 shows a process route diagram demonstrating the method for preparing a cationic β-cyclodextrin functionalized silver nanoparticles (C-β-CD/AgNPs) of the present application.

The present application adopts cationic β-cyclodextrin (C-β-CD) as a reducing agent and a stabilizer to prepare spherical silver nanoparticles having a small particle size and good stability. UV-Vis results show that C-β-CD/AgNPs produce a typical plasmon absorption band of silver nanoparticles at 401 nm; TEM image shows that C-β-CD/AgNPs particles are present in the shape of a sphere and have a particle size of 3-13 nm; XRD results demonstrate the synthesis of face-centered cubic elemental silver; Zeta potential shows that the C-β-CD/AgNPs solution has high stability; FT-IR reveals the modification and reduction effect of the cationic β-cyclodextrin (C-β-CD) to AgNPs. The cationic β-cyclodextrin (C-β-CD) retains the special structure and properties of the cyclodextrin itself. The amine group contained in the structure plays a role in reducing and complexing $Ag^+$ in the synthesis of AgNPs, and plays a certain role in stabilizing nanoparticles in combination with quaternary ammonium groups.

The spherical silver nanoparticles prepared by the present application are cationic β-cyclodextrin-compounded silver particles characterized by nano-microspheres as the unique structure, which have both silver nanoparticles and a cationic β-cyclodextrin structure attached thereto. On the one hand, such silver nanoparticles improve the peptization and stability of silver particles in water, and can be used as a drug-loading unit in combination with other bacteriostatic agents to exert an antibacterial effect. Moreover, the method for preparing silver nanoparticles in the present application is characterized by mild reaction conditions, fast reaction process, easy availability of raw materials and clear product characteristics. The present application studies and expands applications of cationic cyclodextrin (i.e., cationic β-cyclodextrin) in the synthesis of metal nanoparticles. These cationic cyclodextrin-functionalized silver nanoparticles also have application potential in antibiosis, drug delivery and catalysis.

The specific examples below further illustrate cationic β-cyclodextrin and a preparation method and uses thereof, as well as a cationic β-cyclodextrin functionalized silver nanoparticles and a preparation method and uses thereof. This section further explains the present invention with reference to specific examples, but should not be construed as limitation to the present invention. Unless otherwise specified, the technical means used in the examples are conventional means well known to persons of ordinary skill in the art. Unless otherwise specified, the agents, the methods and the devices used herein are conventional agents, methods and devices in the art. The materials used in the following examples are sourced as follows: silver nitrate (analytical grade, Sinopharm Chemical Reagent Co., Ltd.), sodium hydroxide (NaOH) (analytical grade, Sinopharm Chemical Reagent Co., Ltd.), β-cyclodextrin (analytical grade, Admas), p-toluenesulfonyl chloride (TsCl) (analytical grade, GENERAL-REAGENT), 2,3-epoxypropyltrimethylammonium chloride (EPTAC) (analytical grade, Admas), anhydrous ethanol (analytical grade, Sinopharm Chemical Reagent Co., Ltd.), dimethyl sulfoxide (DMSO) (analytical grade, Sinopharm Chemical Reagent Co., Ltd.), and water (laboratory ultrapure water).

Example 1

This example provides a method of preparing cationic β-cyclodextrin, comprising the following steps:
    S1: dissolving 50 g of β-cyclodextrin in 500 mL of a 0.4 M sodium hydroxide solution (0 to 5° C.); adding 35.0 g p-toluenesulfonyl chloride (TsCl) to the sodium hydroxide solution in batches within 5 min and stirring for 30 min; after quickly removing unreacted TsCl via suction filtration, neutralizing the filtrate to pH 8 using 3 M HCl; stirring for 1 h; precipitating the resultant precipitates followed by suction filtration; washing the obtained white precipitate twice with ultrapure water and three times with acetone; and then drying under vacuum at 40° C. to afford toluenesulfonyl-β-cyclodextrin (Ts-β-CD); and
    S2: dissolving 4 g of the toluenesulfonyl-β-cyclodextrin in 20 mL 1,3-propanediamine; reacting at 80° C. for 4 h; after free cooling to room temperature, pouring into ethanol; precipitating the precipitate followed by suction filtration; washing the obtained white precipitate with ethanol and drying under vacuum at 40° C. to afford diaminopropane-β-cyclodextrin (DAP-β-CD); and S3: dissolving 0.6 g 2,3-epoxypropyltrimethylammonium chloride (EPTAC) in 10 mL dimethyl sulfoxide (DMSO); then adding 4.5 g the diaminopropane-β-cyclodextrin (DAP-β-CD); reacting at 80° C. for 4 h; after free cooling to room temperature, pouring into ethanol and precipitating the resultant precipitate followed by suction filtration; washing the obtained white precipitate with ethanol and drying under vacuum at 40° C. to afford cationic β-cyclodextrin (C-β-CD).

Example 2

This example provides a method of preparing a cationic β-cyclodextrin functionalized silver nanoparticles, comprising the following steps:

adding 5 mL of the cationic β-cyclodextrin (prepared in Example 1) solution at a concentration of 0.01 M to 32.5 mL of water, to which 2 mL of a 0.1 M NaOH solution is added with stirring so that the pH is 12; then adding 0.5 mL of a 0.1 M silver nitrate solution, and reacting with stirring at 60° C. for 1 h to afford a cationic β-cyclodextrin functionalized silver nanoparticles (C-β-CD/AgNPs).

Characterization of Properties

1. Determination of the Structure of the Synthesized Product of C-β-CD

The structure of the cyclodextrin-functionalized product was analyzed by $^1$H-NMR and $^{13}$C NMR on a Bruker Avance 600 MHz nuclear magnetic resonance instrument (Bruker BioSpin GmbH) using heavy water as a solvent.

Figure 3:
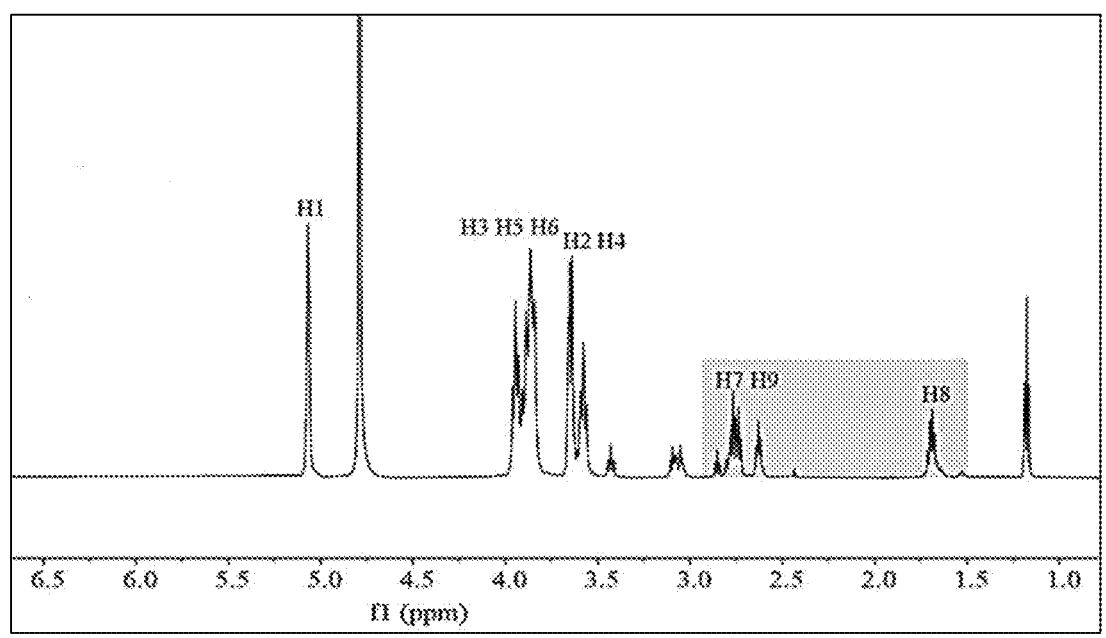
FIG. 3 and FIG. 4 show the $^1H$ NMR and $^{13}C$ NMR spectra of diaminopropane-β-cyclodextrin (DAP-β-CD) in Example 1, respectively.
Figure 4:
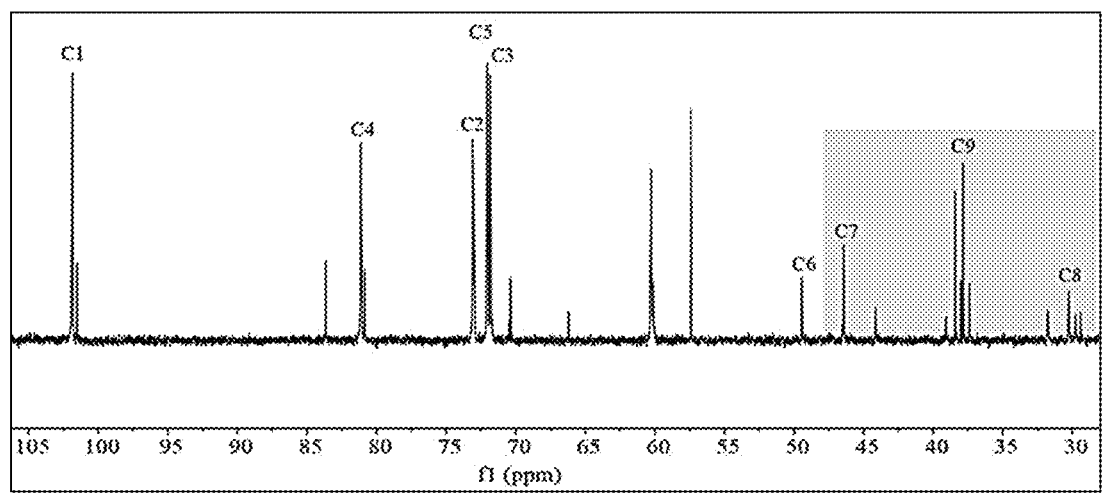
Figure 5:
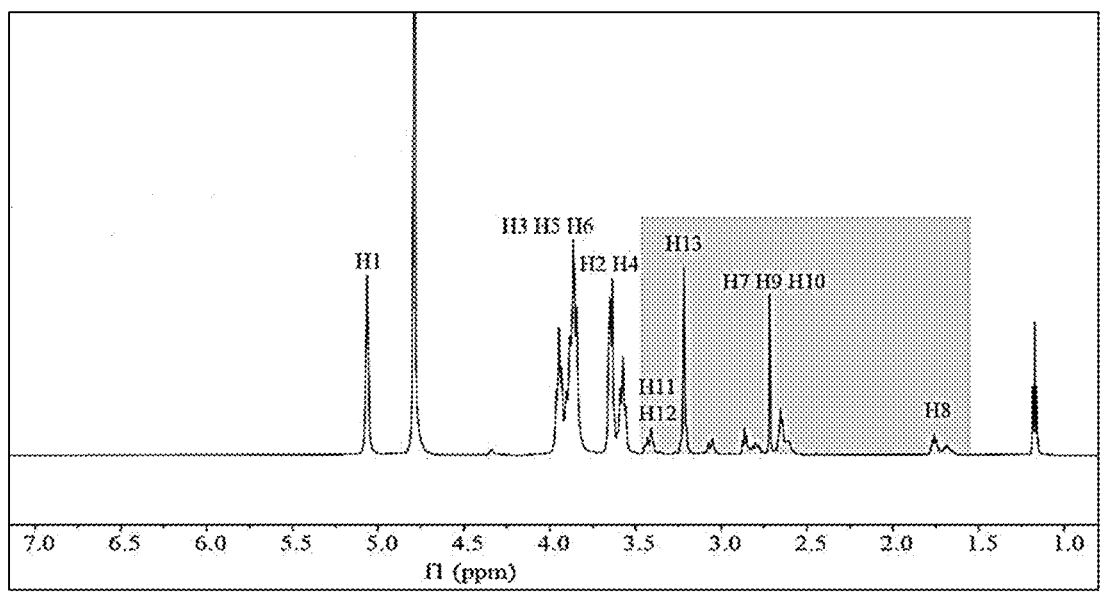
FIG. 5 and FIG. 6 show the $^1H$ NMR and $^{13}C$ NMR spectra of cationic β-cyclodextrin (C-β-CD), respectively.
Figure 6:
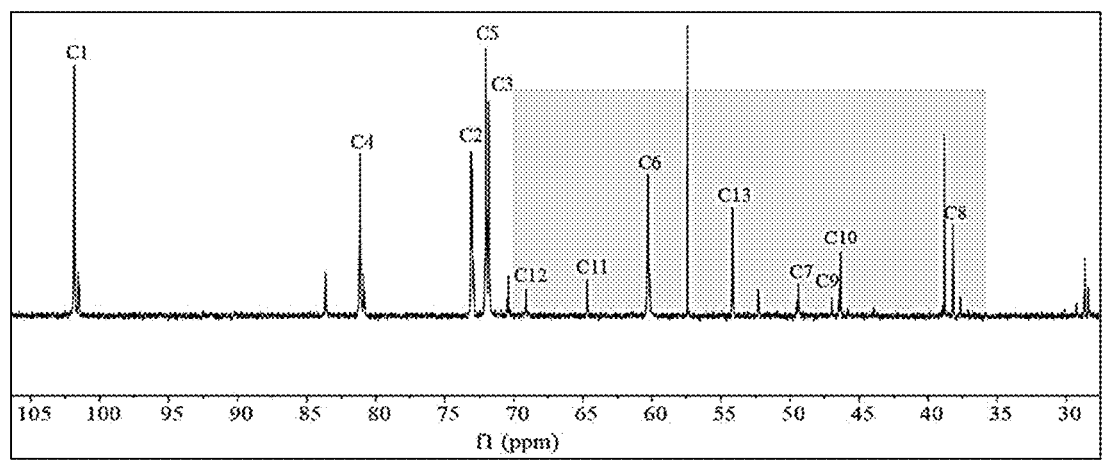

The intermediate product diaminopropane-β-cyclodextrin (DAP-β-CD) prepared in Example 1 and the resulting cationic β-cyclodextrin(C-β-CD) were completely characterized by NMR analysis to determine the specific structures thereof. FIG. 3 and FIG. 4 show $^1$H NMR and $^{13}$C NMR spectra of diaminopropane-β-cyclodextrin (DAP-β-CD), respectively. FIG. 5 and FIG. 6 show $^1$H NMR and $^{13}$C NMR spectra of cationic β-cyclodextrin(C-β-CD), respectively.

Specifically, the C atoms in the intermediate product diaminopropane-3-cyclodextrin(DAP-β-CD) and cationic β-cyclodextrin(C-β-CD) are numbered as follows:

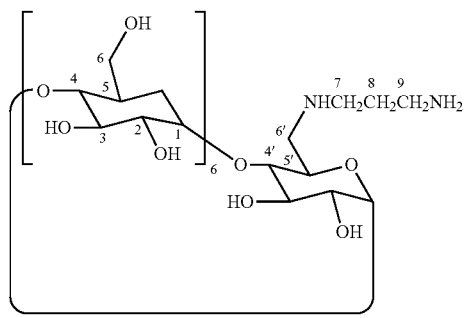

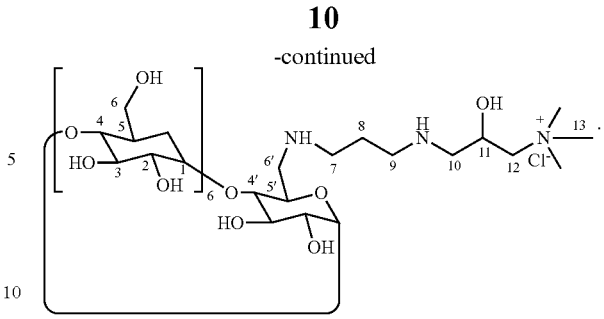

-continued

The $^1$H NMR spectrum in FIG. 3 shows that diaminopropane-β-cyclodextrin (DAP-β-CD) exhibited diaminopropane methylene proton peaks at δ 2.87-2.59 ppm and δ 1.74-1.60 ppm (see the gray box), in addition to the signal peaks of the cyclodextrin glucopyranose units (H1-6). The signal peaks of diaminopropane group C7-9 having chemical shifts at δ 46.43, 30.25, and 37.86 ppm (see the blue box) in the $^{13}$C NMR spectrum of FIG. 4 also verify the substitution of β-CD with diaminopropane.

The $^1$H NMR spectrum in FIG. 5 shows that cationic β-cyclodextrin (C-β-CD) exhibited proton peaks (see the gray box) of diaminopropane group and quaternary ammonium cationic group moieties, wherein the cationic group proton peaks of H11-12 were at δ 3.47-3.35 ppm; the methylene proton peaks of H7 and H9-10 connected to the N atom were at δ 2.47-3.35 ppm; the methylene proton peak of H8 in the diaminopropane group was at δ 1.83 and the characteristic single peak of methyl in the quaternary ammonium salt branch chain was at δ 3.24. In the $^{13}$C NMR spectrum of FIG. 6, the gray box demonstrates carbon spectrum signal peaks of the modification groups, including the C7-9 signal peaks of the diaminopropane modification moiety in C-β-CD with chemical shifts at δ 49.50, 38.19, and 46.97 respectively, and the C10-13 signal peaks of the quaternary ammonium cationic group moiety with chemical shifts at δ 46.32, 64.68, 69.12, and 54.15, respectively. The characterization data and analysis results of 1-CD derivatives are consistent with the product structure, indicating that the product has been successfully synthesized.

2. Characterization of the Cationic β-Cyclodextrin Functionalized Silver Nanoparticles (C-β-CD/AgNPs)

Figure 7:
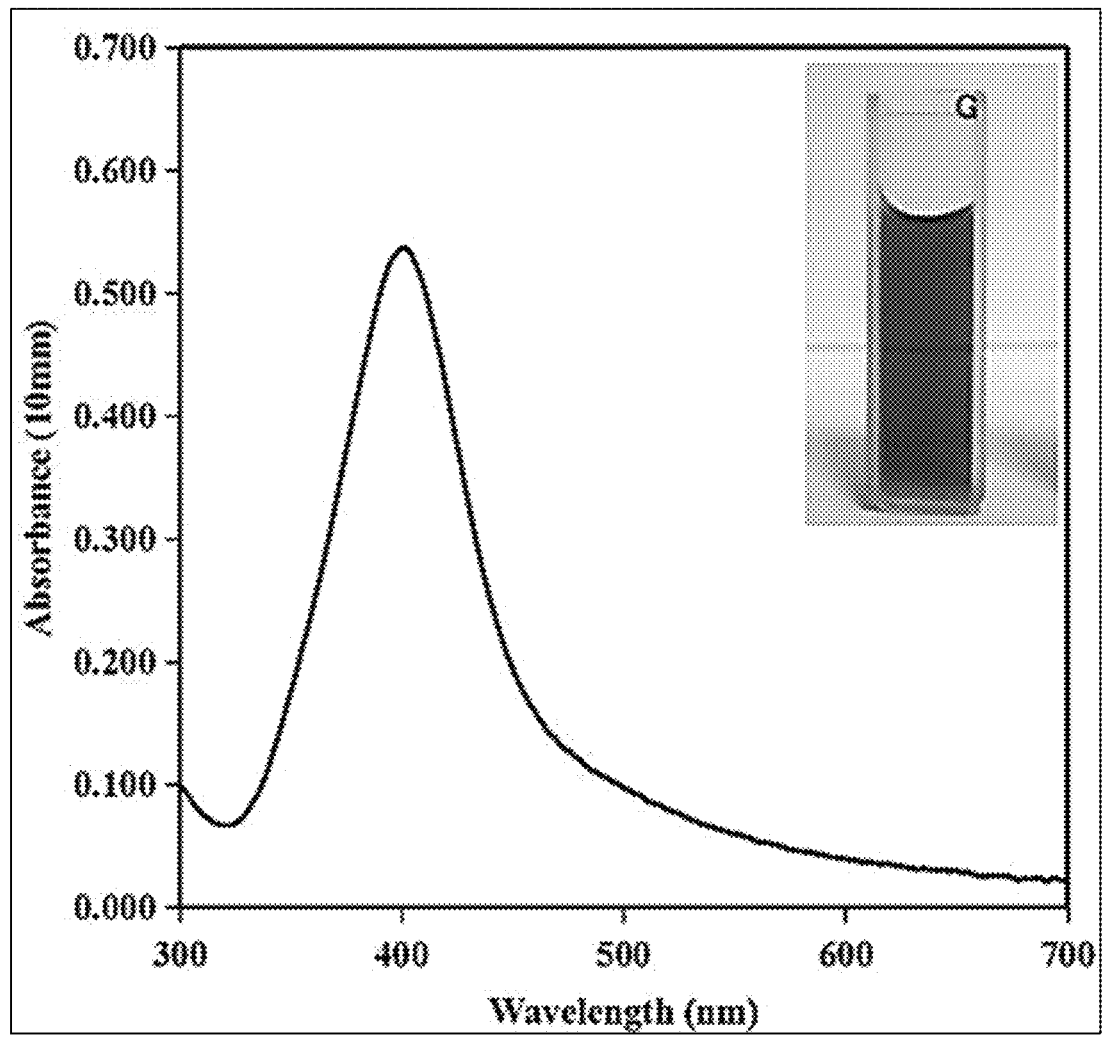
FIG. 7 is a UV-visible absorption spectrum of the cationic β-cyclodextrin functionalized silver nanoparticles solution in Example 2.

In the process of preparing silver nanoparticles in Example 2, with the addition of the $AgNO_3$ solution, the solution changed from colorless to gray-green and finally turned yellowish brown as the reaction time increased, indicating the generation of silver nanoparticles. N60 Imlen ultra-trace UV-visible spectrophotometer (Beijing Nuohuicheng Technology Co., Ltd.) was used to characterize the surface plasmon effect of AgNPs. Ultrapure water was used as the blank group. The UV-visible absorbance spectrum of the AgNPs solution was determined in the wavelength range of 300-600 nm. The visible light spectroscopic analysis of the silver nanoparticle solution was performed using a UV-visible spectrophotometer. Absorption peaks characterize the surface plasmon effect of silver nanoparticles. The morphology of AgNPs is related to the position of the maximum absorption peak. The study demonstrates that the absorption peak at 400 nm indicates that the prepared nanoparticles are present in a substantially spherical shape. The UV-Vis absorbance spectrum of AgNPs is shown in FIG. 7 (the image inserted in FIG. 7 is a photo of the AgNPs solution). The UV-Vis results demonstrate that AgNPs have a typical plasmon absorption band at 402 nm, indicating the successful preparation of spherical AgNPs.

Figure 8:
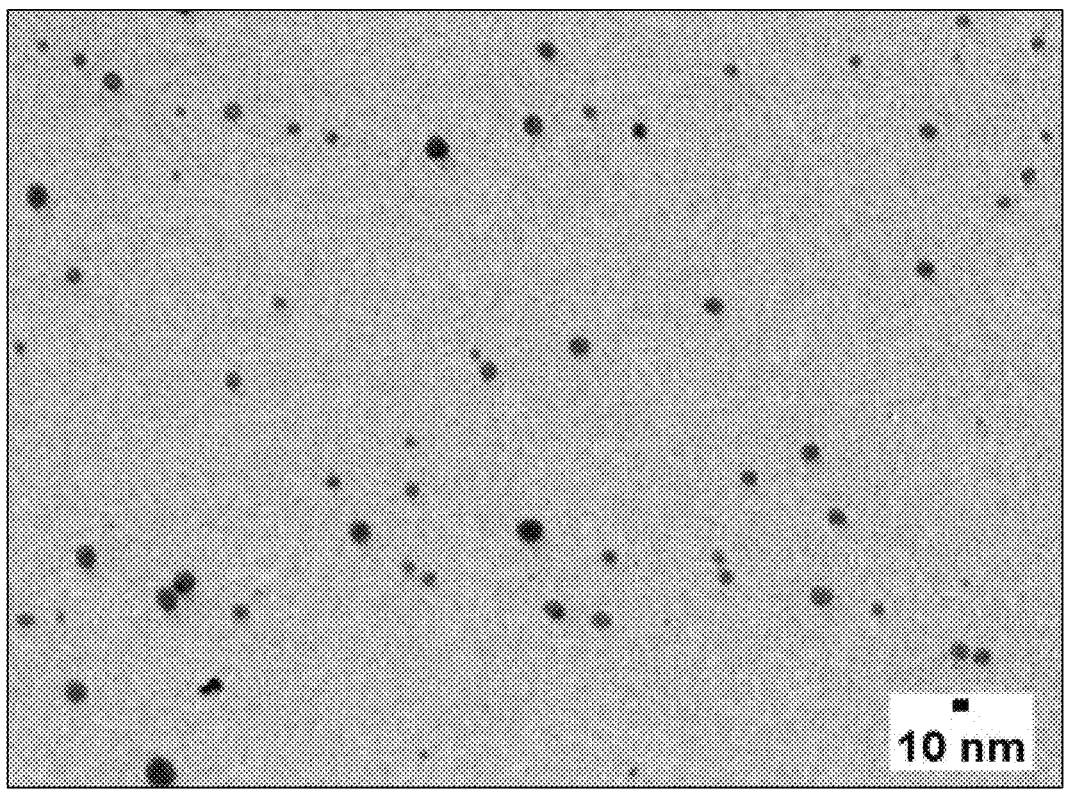
FIG. 8 shows a TEM image of C-β-CD/AgNPs prepared in Example 2.
Figure 9:
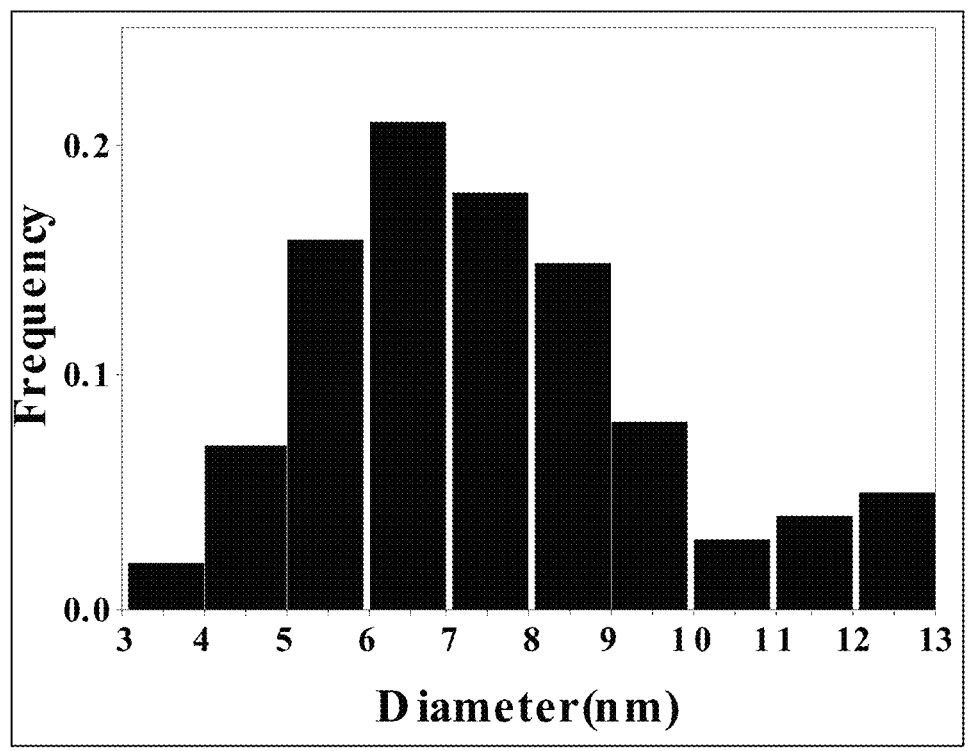
FIG. 9 is a diagram illustrating the particle size distribution of C-β-CD/AgNPs prepared in Example 2.

The AgNPs solution prepared in Example 2 was dropwise added onto the surface of a film supported-copper grid for electron microscopy, and was observed in aspects of AgNPs particle morphology, particle size, and dispersion using a JEM-1400 transmission electron microscope (JEOL Co., Ltd.) at an accelerating voltage of 80 Kv after free drying. The prepared C-β-CD/AgNPs were characterized in morphology and size by virtue of TEM and were observed in terms of size, quantity and distribution. The TEM image is shown in FIG. 8. 100 C-β-CD/AgNPs were randomly selected and measured using ImageJ to obtain the particle size distribution, as shown in FIG. 9. In the TEM image, it is observed that the nanoparticles are in the morphology of a substantial sphere, and have a narrow particle size distribution concentrated in the range of 3-13 nm, and an average particle size of 7.60 f 2.14 nm.

Fourier transform infrared spectroscopy is an important tool for studying biomolecules that coat and stabilize nanoparticles because elemental silver itself does not have characteristic infrared absorption peaks. In order to explore the interaction between cyclodextrin and AgNPs, C-β-CD and C-β-CD/AgNPs were assessed by FT-IR.

Nicolet 6700 Fourier transform infrared spectrometer (Thermo Fisher Scientific Co., Ltd.) was used to characterize the compositions of AgNPs and C-β-CD. The AgNPs solution prepared in Example 2 was centrifuged and washed before dispersing in an aqueous solution, and freeze-dried to afford an AgNPs powder; after the powder was tableted with potassium bromide, 32 scans were performed in a resolution of 4 $cm^1$ and 400-4000 $cm^{-1}$. Specifically, FIG. 10 shows FT-IR spectra of the C-β-CD functionalized silver nanoparticles (C-β-CD/AgNPs) and the cationic β-cyclodextrin (C-β-CD) prepared in Example 2.

Figure 10:
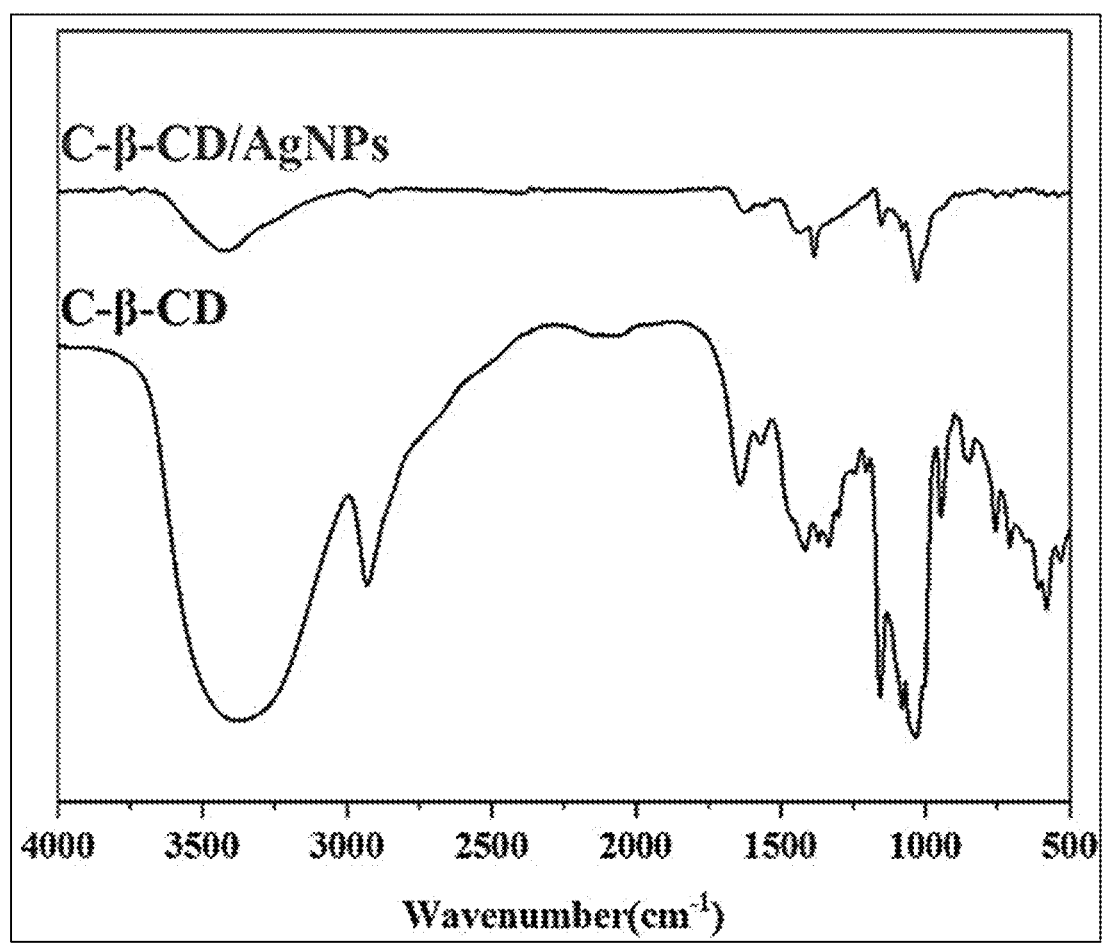
FIG. 10 shows FT-IR spectra of the cationic 1-cyclodextrin functionalized silver nanoparticles (C-β-CD/AgNPs) and the cationic β-cyclodextrin (C-β-CD) prepared in Example 2.

FIG. 10 shows that the FT-IR spectra of the C-β-CD functionalized silver nanoparticles (C-β-CD/AgNPs) and the cationic β-cyclodextrin (C-β-CD) are highly similar. In the spectrum of C-β-CD/AgNPs, the N—H deformation vibration peak of C-β-CD itself at 1570 $cm^{-1}$ was attenuated to a certain extent in addition to the characteristic absorption peaks of the C-β-CD glucopyranose units, indicating that the amine group interacts with $Ag^+$ A $COO^-$ stretching vibration at 1626 and 1383 $cm^{-1}$ was generated via the Ag—$COO^-$ interaction. The hydroxyl groups of C-β-CD as a reducing agent reduced $Ag^+$ to AgNPs, and itself was oxidized to carboxylic acid, indicating that C-β-CD is coated on the surface of AgNPs and interacts with AgNPs.

Figure 11:
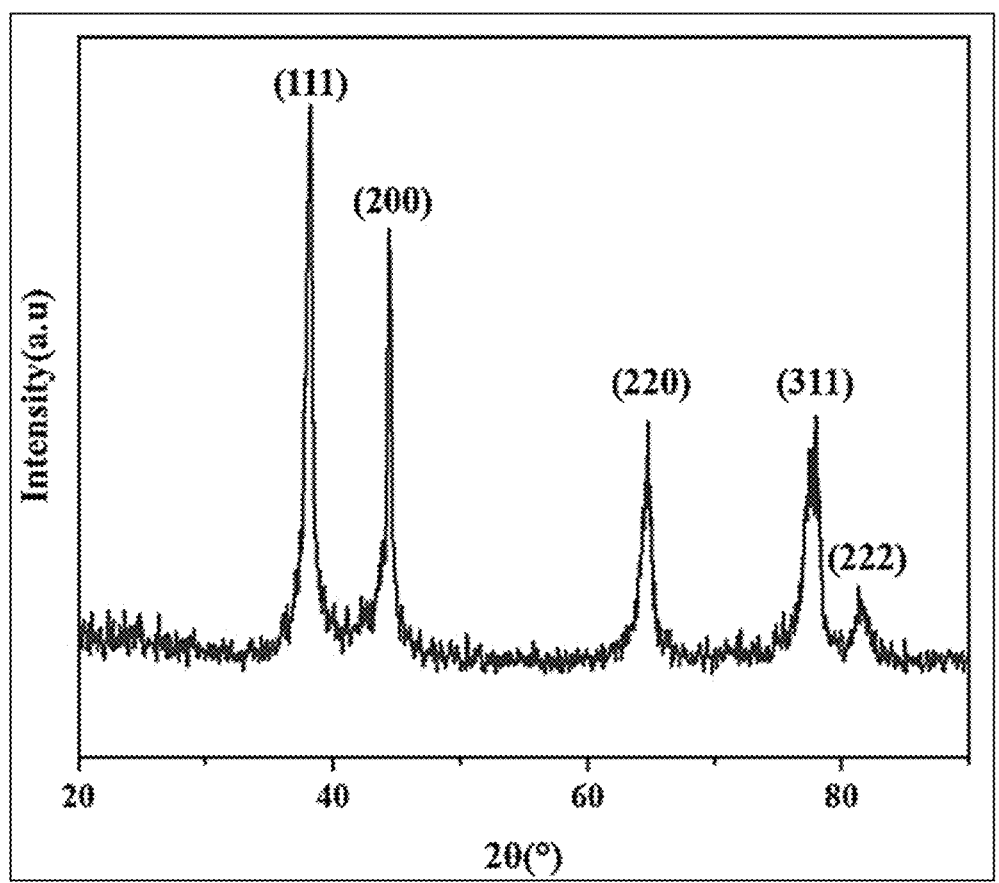
FIG. 11 shows XRD patterns for the cationic β-cyclodextrin functionalized silver nanoparticles (C-β-CD/AgNPs) prepared in Example 2.

The C-β-CD functionalized silver nanoparticles (C-β-CD/AgNPs) prepared in Example 2 were subject to XRD assay using XD6 X-ray diffractometer (Beijing Puxi General Instrument Co., Ltd.), working voltage 40 kV, current 30 mA, CuKα rays, scanning speed 5°/min, and scanning range from 20° to 90°. The results are shown in FIG. 11.

The XRD technique was used to characterize the crystal structure of C-β-CD/AgNPs. The XRD spectrum of C-β-CD/AgNPs demonstrates sharp diffraction peaks, indicating that AgNPs have good crystallinity. The diffraction peaks at 38.18°, 44.40°, 64.80°, 77.96°, and 81.52°(FIG. 11) correspond to face-centered cubic crystalline singlets (111), (200), (220), (311) and (222) crystallographic planes of silver, further confirming the presence of C-β-CD/AgNPs.

Measurement of Zeta Potential for Testing

The stability of AgNPs in an aqueous suspension is very important, and AgNPs usually have high stability at a Zeta potential of less than −25 mV or greater than +25 mV. 1 mL the resulting AgNPs solution in Example 2 was taken into a sample cell, and Zetasizer Nano S90, a Malvern particle size potential analyzer (Malvern Panalytical Ltd., UK), to determine a Zeta potential of the silver nanoparticle suspension. The surface charge of C—β-CD/AgNPs was determined to be −34.43±0.84 mV, indicating that AgNPs have good stability. Positive charges carried by the amine group and quaternary ammonium groups in C-β-CD can effectively increase charge repulsions between nanoparticles, play a role in stabilization to some degree in the synthesis of AgNPs, and prevent the agglomeration of AgNPs.

3. Drug-Loading Application Examples of C-β-CD 3.1 C-β-CD Encapsulating the Volatile Bacteriostatic Agent Thymol Thymol (2-isopropyl-5-methylphenol) is a monoterpene phenol that is mainly found in plant essential oils such as thyme oil, oregano oil, and clove basil oil. It has been proven to have a variety of biological activities, including antioxidant, anti-inflammatory, analgesic and anti-tumor activities, especially antibacterial properties, that is, it has an antibacterial effect on and sensitivity to various types of bacteria and fungi. The significant biological activities allow thymol to attract great attention in biomedical applications. However, the drawbacks of thymol including low water solubility, high volatility and strong irritation limit the effective development and application to a great extent. Therefore, encapsulation with some drug carriers improves water solubility and reduces volatilization and mucosal irritation, and hence is of great significance to expand the application scope.

0.656 g of the cationic β-cyclodextrin (C-β-CD) prepared in Example 1 was weighed and added with 10 mL distilled water until completely dissolution. An anhydrous ethanol solution containing 0.075 g thymol (2 mL in total) was added. The mixture was magnetically stirred in a water bath at 40° C. for 2 h. After completion, the mixture was filtered with a 0.45 μm microporous membrane. The resulting solution was freeze-dried for 24 h to afford a thymol/C-β-CD inclusion complex.

Figure 12:
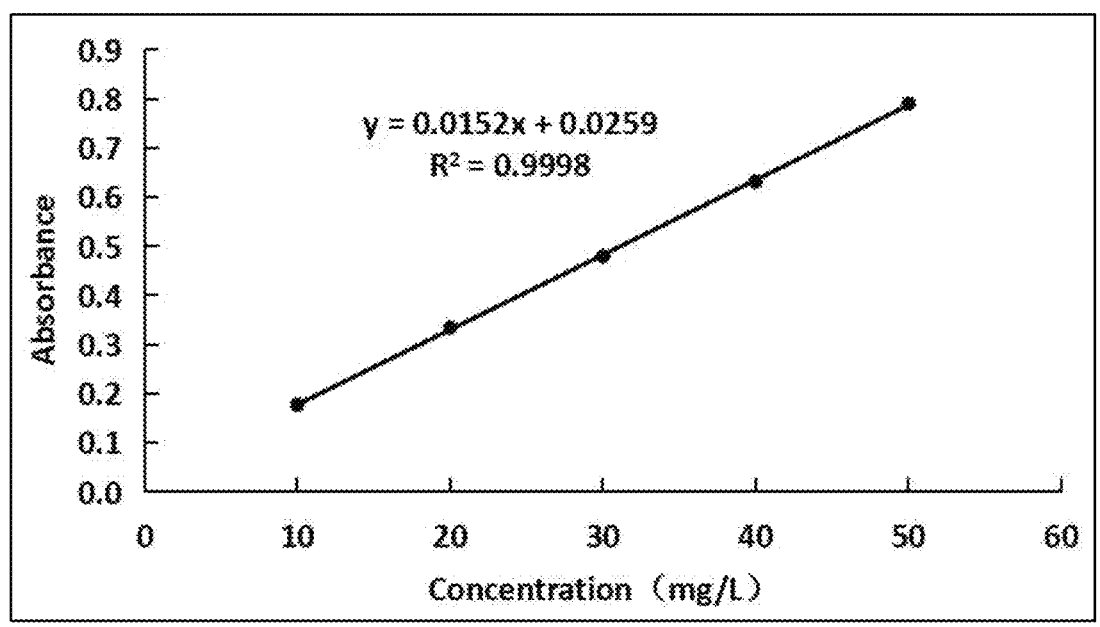
FIG. 12 is a standard curve for the thymol standard solution.

15 mg of analytically pure thymol was weighed and dissolved in anhydrous ethanol, and the volume was adjusted to 10 mL to prepare a 1500 mg/L stock solution. A proper amount of the stock solution was taken and diluted with anhydrous ethanol into a series of standard solutions at a concentration of 50, 40, 30, 20, and 10 mg/L. In the optimal absorption wavelength, an absorbance A of the above series of standard solutions was determined. A standard curve was drawn with a thymol concentration (mg/L) as an abscissa and A as an ordinate. The results are shown in FIG. 12.

0.1 g of the thymol/C-β-CD inclusion complex as prepared above was weighed and added into a 25 mL volumetric flask, added with anhydrous ethanol to dilute to the mark, and sonicated for 30 min. A proper amount of the solution was taken and centrifuged. The supernatant was diluted by a certain multiple. The absorbance A of the solution at 278 nm was determined, and taken into the regression equation to calculate the thymol content in the inclusion complex.

$$\text{Inclusion Rate} = \frac{\text{the compound content actually comprised in the inclusion complex}}{\text{the compound content added before inclusion}} * 100\%$$

Taking a thymol solution concentration (mg/L) as the abscissa and A as the ordinate, the regression equation Y=0.0152X+0.0259 ($R^2$=0.9998) was obtained. The thymol solution exhibited a good linear relationship in the range of 10-50 mg/L.

By testing, the inclusion rate of cationic cyclodextrin (i.e., cationic β-cyclodextrin (C-β-CD) for thymol in the inclusion complex prepared according to the above method was 63.55%.

Figure 13:
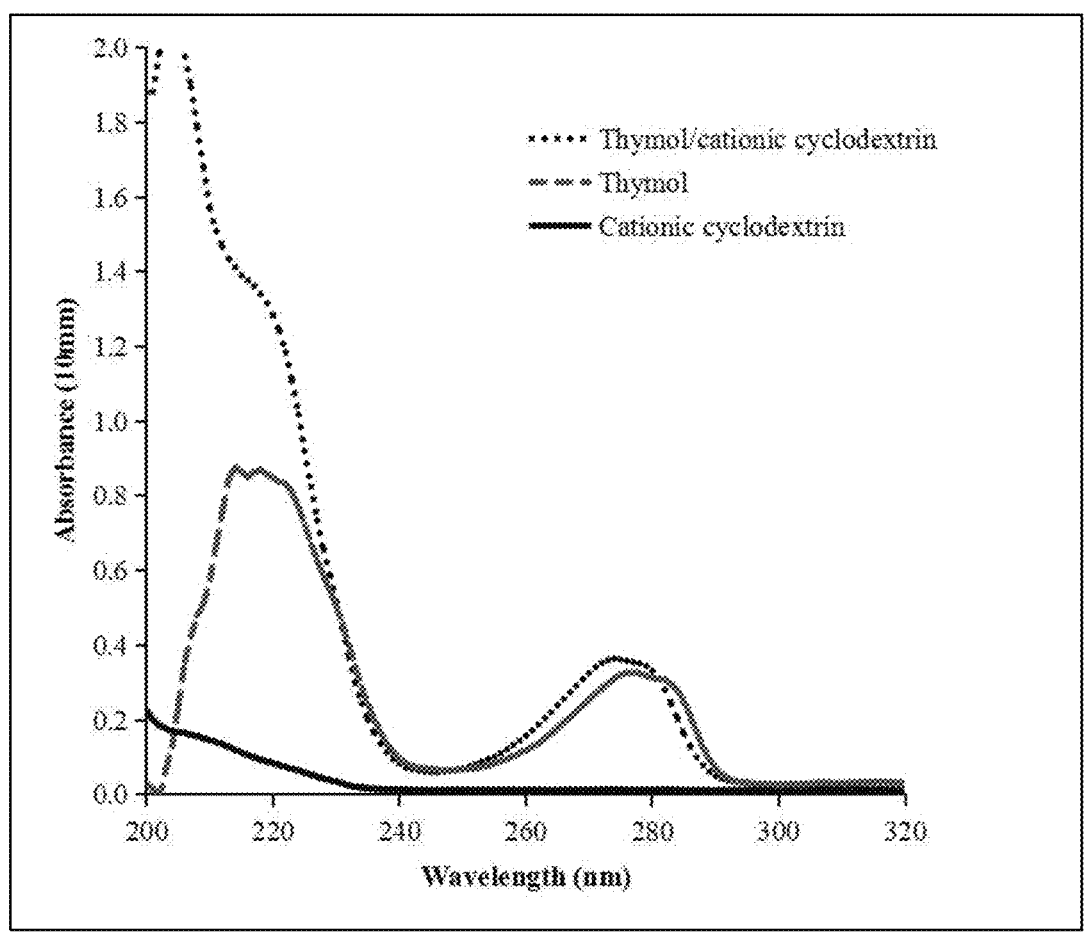
FIG. 13 shows UV absorption spectra of thymol, and a thymol/C-β-CD inclusion complex.

A proper amount of the thymol/C-β-CD inclusion complex was weighed, added with water for dissolution, and brought to volume in a 10 mL volumetric flask. Scanning was performed at a wavelength of 200-600 nm. Spectroscopy scans of the aqueous solution of cationic cyclodextrin (i.e., the cationic β-cyclodextrin (C-β-CD) solution) and the anhydrous ethanol solution of thymol at the same wavelength serve as control groups. Whether an inclusion complex is formed was judged by comparing the differences in the UV spectrum of each sample. The results are shown in FIG. 13. In FIG. 13, the cationic cyclodextrin is cationic β-cyclodextrin (C-β-CD), and thymol/cationic cyclodextrin is the thymol/C-β-CD inclusion complex. The results show that C-β-CD itself has no characteristic UV absorption peak. Characteristic UV absorption peaks were observed in the UV absorption spectrum of the inclusion product, similar to the spectrum of the guest molecule thymol, wherein the characteristic UV absorption peak of thymol at 223 nm had significant change, mainly embodied in a significant increase in abundance and notable movement of the maximum absorption wavelength in the shortwave direction, and the characteristic UV absorption peak at 278 nm moved slightly in the shortwave direction while the abundance and peak shape remained basically unchanged.

Figure 14:
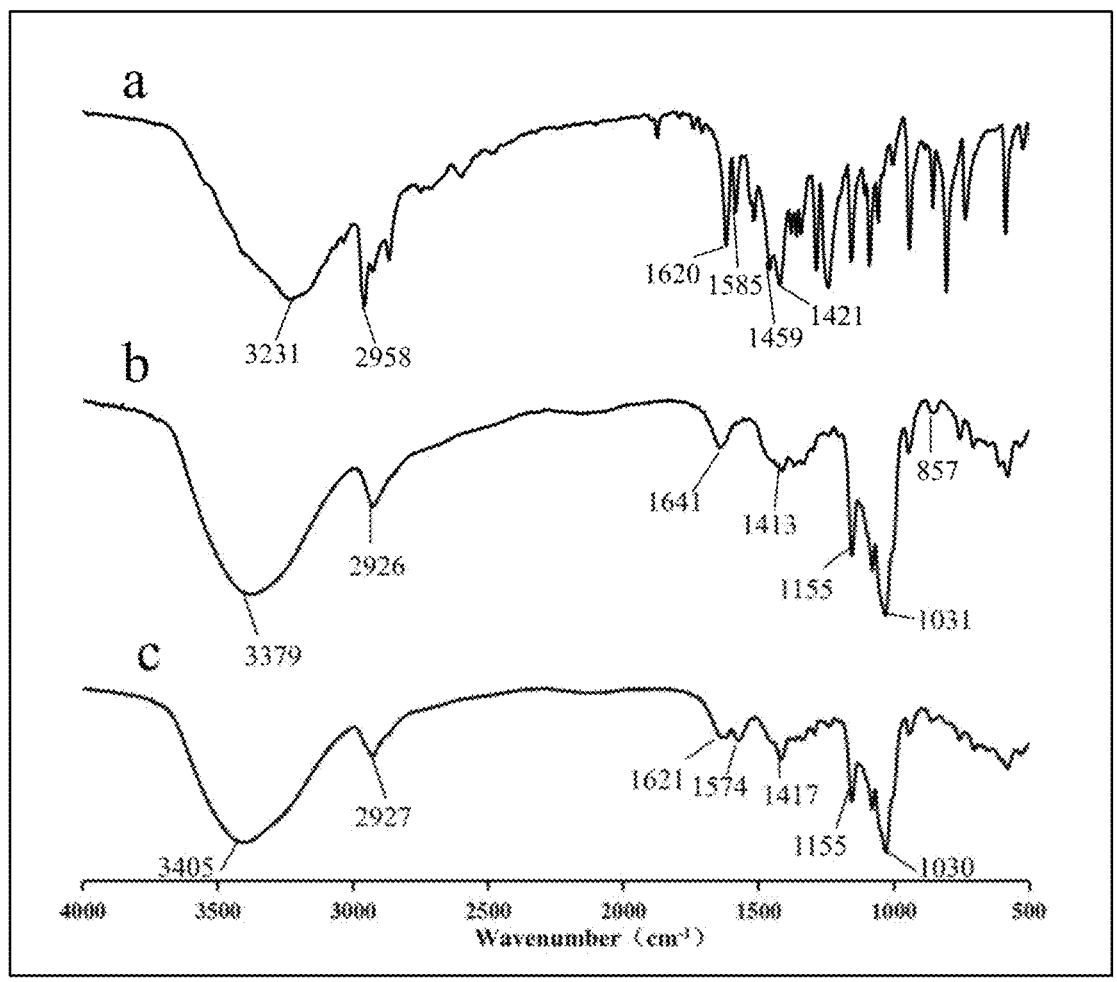
FIG. 14 shows FT-IR spectra of thymol, C-β-CD and a thymol/C-β-CD inclusion complex.

Thymol, C-β-CD and the thymol/C-β-CD inclusion complex were taken as samples, respectively. Each sample was tableted with potassium bromide and assayed in the range of 400-4000 $cm^{-1}$. The differences in the FT-IR spectra of thymol, C-β-CD and the inclusion complex were compared to determine whether an inclusion complex is formed. The FT-IR spectra are shown in FIG. 14. In FIG. 14, a represents thymol, b represents C-β-CD, and c represents a thymol/C-β-CD inclusion complex.

In the infrared spectrum of thymol (spectrum a), because the structure contains phenolic hydroxyl and phenyl groups, there were —O—H stretching vibration absorption bands at 3600-3200 $cm^{-1}$, and characteristic absorption peaks of benzene ring at 1620 $cm^{-1}$, 1585 $cm^{-1}$ and 1517 $cm^{-1}$. C-β-CD (spectrum b) exhibited characteristic absorption peaks of sugars, —O—H stretching vibration at 3000-3500 $cm^{-1}$, —C—H stretching vibration at 2926 $cm^{-1}$, and asymmetric stretching vibration of the —C-β-C-glycosidic bond at 1031 $cm^{-1}$. The amine group of C-β-CD had an absorption peak similar to —O—H at 3300 $cm^{-1}$, which may be masked by the —O—H group. The infrared spectrum of the thymol/C-β-CD inclusion complex (spectrum c) was similar to that of C-β-CD. Some of the characteristic absorption peaks of thymol were significantly reduced and the peak shapes were broadened. These changes upon the interaction between the thymol group and cyclodextrin indicate that an inclusion complex has been formed.

3.2 C-β-CD Encapsulating the Volatile Tyrosinase Inhibitor Cinnamaldehyde

Tyrosinase is a copper-containing oxidoreductase whose active center consists of two metallic copper ions connected via an endogenous bridge, and three histidine residues on each ion. The combination of a substrate (such as tyrosine and levodopa) and an enzyme active center mainly works through a phenolic hydroxyl group, which is oxidized into a carbonyl group.

In the presence of oxygen free radicals, tyrosinase catalyzes the oxidation of tyrosine to form levodopa (demonstrating monophenolase activity). This reaction proceeds slowly at first, but accelerates after the formation of dopa; then levodopa is converted into red dopaquinone (demonstrating diphenolase activity) in the catalysis of tyrosinase; dopaquinone forms melanin in a multimerization reaction, which is transported to nearby keratinocytes through dendrites of melanocytes and hence results in pigmentation in epidermis.

Tyrosinase is a rate-limiting enzyme in melanin synthesis. Studies in recent years have shown that tyrosinase inhibitors can be used as whitening agents in cosmetics, preservatives in food, and pesticides in crops. Cinnamaldehyde is a potent tyrosinase inhibitor obtained from medicinal plants such as cassia twig and cinnamon. However, its drawbacks of low water solubility, high volatility and strong odor have significantly limited the development and application thereof in cosmetics, food preservation and other related fields. Therefore, encapsulation with some drug carriers improves water solubility and reduces evaporation loss, and hence is of great significance to expand the application scope.

0.656 g the cationic β-cyclodextrin (C-β-CD) prepared in Example 1 was weighed and added with 10 mL distilled water until completely dissolution. An anhydrous ethanol solution containing 0.066 g cinnamaldehyde was added slowly. The mixture was magnetically stirred in a water bath at 45° C. for 4 h. After completion, the mixture was filtered with a 0.45 μm microporous membrane. The resulting solution was freeze-dried for 24 h to afford a cinnamaldehyde/C-β-CD inclusion complex.

Figure 15:
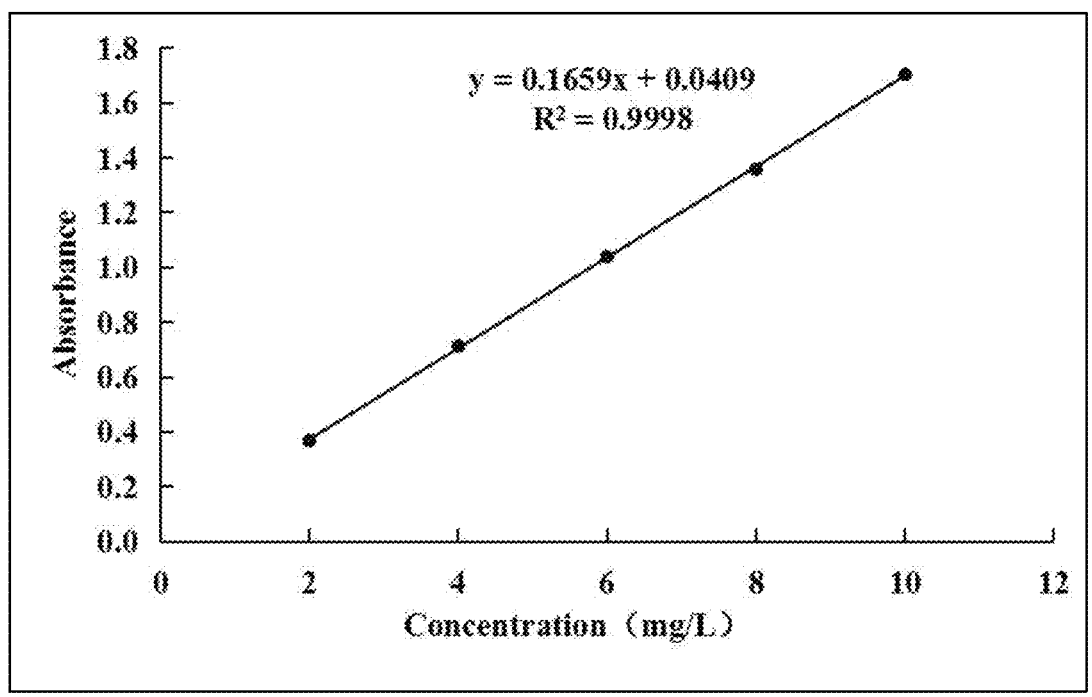
FIG. 15 is a standard curve for a cinnamaldehyde standard solution.

10 mg analytically pure cinnamaldehyde was weighed and dissolved in anhydrous ethanol, and the volume was adjusted to 10 mL to prepare a 1000 mg/L stock solution. A proper amount of the stock solution was taken and diluted with anhydrous ethanol into a series of standard solutions at a concentration of 2, 4, 6, 8, and 10 mg/L. In the optimal absorption wavelength, the absorbance A of the above series of standard solutions was determined. A standard curve was drawn with a cinnamaldehyde concentration (mg/L) as the abscissa and A as the ordinate. The results are shown in FIG. 15.

Taking a cinnamaldehyde concentration (mg/L) as the abscissa and A as the ordinate, the regression equation $Y=0.1659X+0.0409$ ($R^2=0.9998$) was obtained. The cinnamaldehyde solution exhibited a good linear relationship in the range of 2-10 mg/L.

0.01 g of the C-β-CD inclusion complex of cinnamaldehyde was weighed and added into a 25 mL volumetric flask, added with anhydrous ethanol to dilute to the mark, and sonicated for 30 min. A proper amount of the solution was taken and centrifuged. The supernatant was taken and diluted by a certain multiple. The absorbance A of the solution was determined at 287 nm and taken into the regression equation to calculate the cinnamaldehyde content in the inclusion complex (see the previous example for the conversion formula). By testing, in the inclusion complex prepared by the saturated aqueous solution method, the inclusion rate of C-β-CD for cinnamaldehyde was 21.55%.

Figure 16:
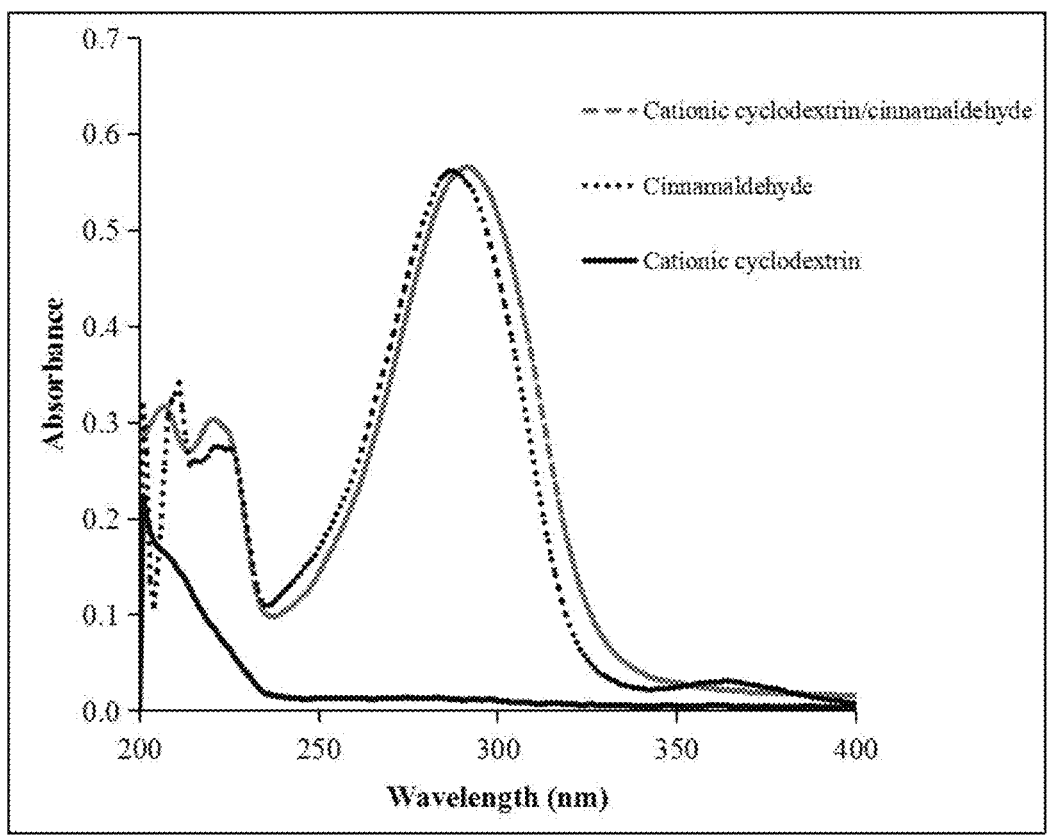
FIG. 16 shows UV spectra of a C-β-CD inclusion complex of cinnamaldehyde.

A proper amount of the cinnamaldehyde/C-β-CD inclusion complex was weighed, added with water for dissolution, and brought to volume in a 10 mL volumetric flask. Scanning was performed at a wavelength of 200-600 nm. Spectroscopy scans of the aqueous solution of cyclodextrin (i.e., the cationic β-cyclodextrin (C-β-CD) solution) and the anhydrous ethanol solution of cinnamaldehyde at the same wavelength serve as control groups. Whether an inclusion complex is formed was judged by comparing the differences in the UV spectrum of each sample. The results are shown in FIG. 16. In FIG. 16, the cationic cyclodextrin is cationic β-cyclodextrin (C-β-CD), and cationic cyclodextrin/cinnamaldehyde is the cinnamaldehyde/C-β-CD inclusion complex. The results show that C-β-CD itself has no characteristic UV absorption peak. Characteristic UV absorption peaks were observed in the UV absorption spectrum of the inclusion product, similar to the spectrum of the guest molecule cinnamaldehyde, wherein the characteristic UV absorption peak of cinnamaldehyde at 230 nm had no significant change, and the characteristic UV absorption peak at 280 nm moved slightly in the longwave direction while the abundance and peak shape remained basically unchanged.

Figure 17:
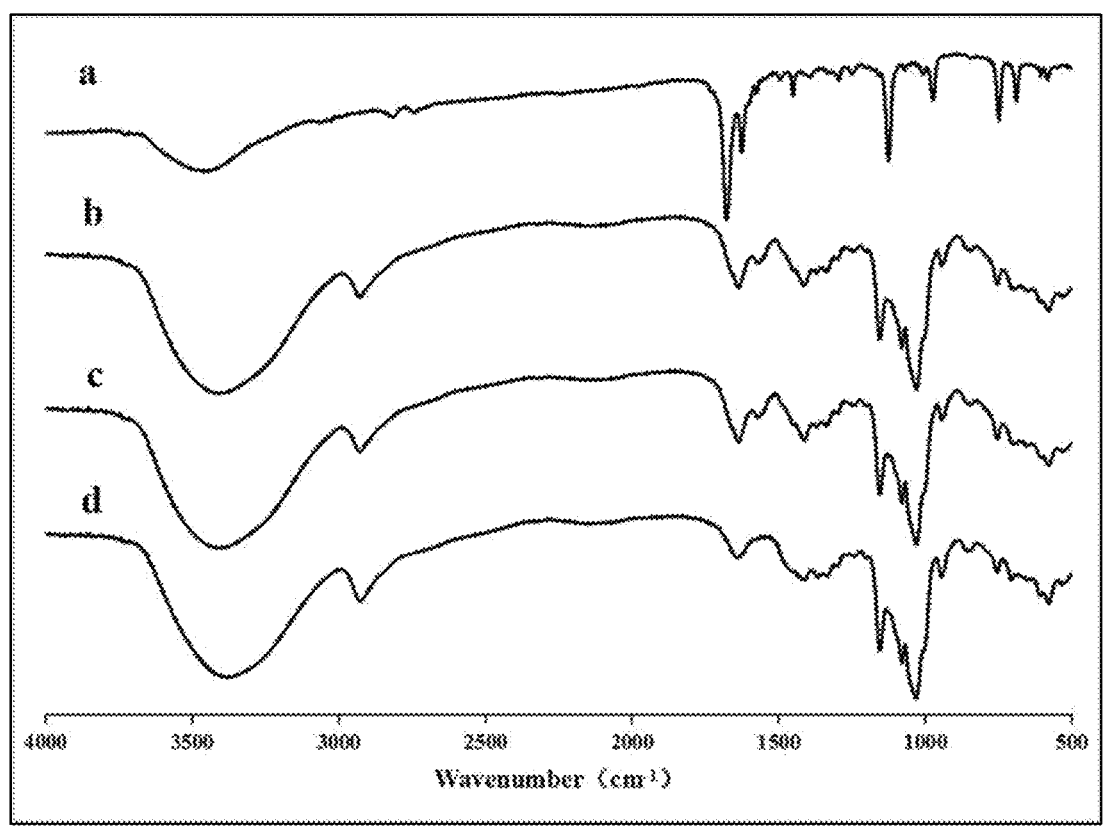
FIG. 17 shows FT-IR spectra of cinnamaldehyde, C-β-CD, a C-β-CD inclusion complex of cinnamaldehyde and a physical mixture of C-β-CD and cinnamaldehyde.

Cinnamaldehyde, C-β-CD, the C-β-CD inclusion complex of cinnamaldehyde and the physical mixture of C-β-CD and cinnamaldehyde were taken as samples, respectively. Each sample was tableted with potassium bromide and assayed in the range of 400-4000 cm$^{-1}$. The differences in the FT-IR spectra of cinnamaldehyde, cyclodextrin, the inclusion complex and the physical mixture were compared to determine whether an inclusion complex is formed. The results are shown in FIG. 17. In FIG. 17, a represents cinnamaldehyde, b represents a C-β-CD inclusion complex of cinnamaldehyde, c represents a physical mixture of C-β-CD and cinnamaldehyde and d represents C-β-CD.

4. Examples of Drug-Loading Application of Cationic β-Cyclodextrin Functionalized Silver Nanoparticles (C-β-CD/AgNPs)

According to the process in the foregoing Example 2, 5 mL the cationic β-cyclodextrin (C-β-CD) (prepared in Example 1) solution at a concentration of 0.01 M was added to 32.5 mL water, to which 2 mL a 0.1 M NaOH solution was added with stirring so that the pH was 12; then 0.5 mL a 0.1 M silver nitrate solution was added and reacted with stirring at 60° C. for 1 h to afford a C-β-CD/AgNPs solution. The solution was cooled down at room temperature before centrifugation, dispersed in an aqueous solution after washing, and freeze-dried to afford the C-β-CD/AgNPs powder.

100 mg of the C-β-CD/AgNPs powder obtained by freeze-drying was weighed, redissolved in 5 mL deionized water, and vortexed to form a light brown solution. An excess anhydrous ethanol solution of thymol was added dropwise to the light brown solution. The mixture was magnetically stirred in a water bath at 40° C. for 2 h, and centrifuged after the reaction was completed. The precipitate at the bottom of the centrifuge tube was collected, and freeze-dried for 24 h to afford a thymol-encapsulated C-β-CD/AgNPs powder.

Figure 18:
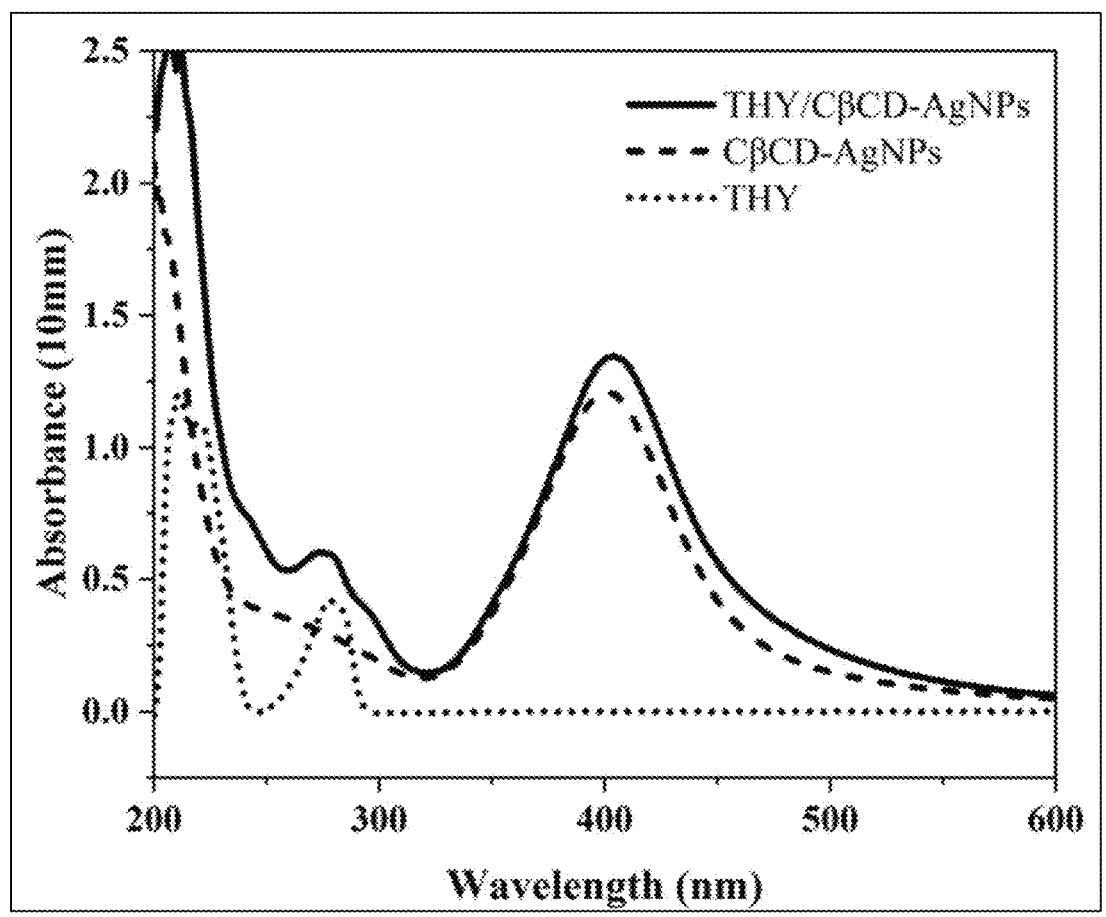
FIG. 18 shows UV absorption spectra of thymol, C-β-CD-AgNPs and a thymol/C-β-CD-AgNPs inclusion complex.

Analysis of UV-visible absorbance spectra: N60 Imlen ultra-trace UV-visible spectrophotometer (Beijing Nuohuicheng Technology Co., Ltd.) was used to record UV-visible absorbance spectra of thymol (THY), a C-β-CD/AgNPs solution and a THY/C-β-CD/AgNPs (a thymol-encapsulated C-β-CD/AgNPs) solution. THY was dissolved in anhydrous ethanol to prepare a THY ethanol solution at a concentration of 25 μg/ml; the C-β-CD/AgNPs and THY/C-β-CD/AgNPs solutions were prepared by diluting 10 times with deionized water. The UV-visible absorbance spectra of the solutions were determined in the wavelength range of 200-600 nm. The results are shown in FIG. 18. In FIG. 18, THY/C-β-CD/AgNPs represents the THY/C-β-CD/AgNPs solution, and C-β-CD/AgNPs represents the C-β-CD/AgNPs solution.

FIG. 18 shows that characteristic UV absorption peaks were observed at 223 nm and 275 nm in the UV-visible absorbance spectrum of the THY/C-β-CD/AgNPs solution, similar to the spectrum of the guest molecule thymol; at the same time, a characteristic peak at 410 nm was present similar to the spectrum of C-β-CD/AgNPs, demonstrating that C-β-CD/AgNPs retains the drug-loading function of cationic cyclodextrin.

Preparation of a silver nanoparticle sample for control: 0.1 mol/L AgCl was dissolved in 16 mL of an ammonia solution at a mass concentration of 25% with continuous stirring, and an aqueous solution of 0.1 mol/L vitamin C was added dropwise. It was seen that the transparent solution turned into yellow, gray, and finally yellowish brown. The solution was then filtered, and the precipitate was washed repeatedly with double-distilled water, dispersed in double-distilled water, and freeze-dried for 24 h to afford silver nanoparticles prepared from vitamin C.

Figure 19:
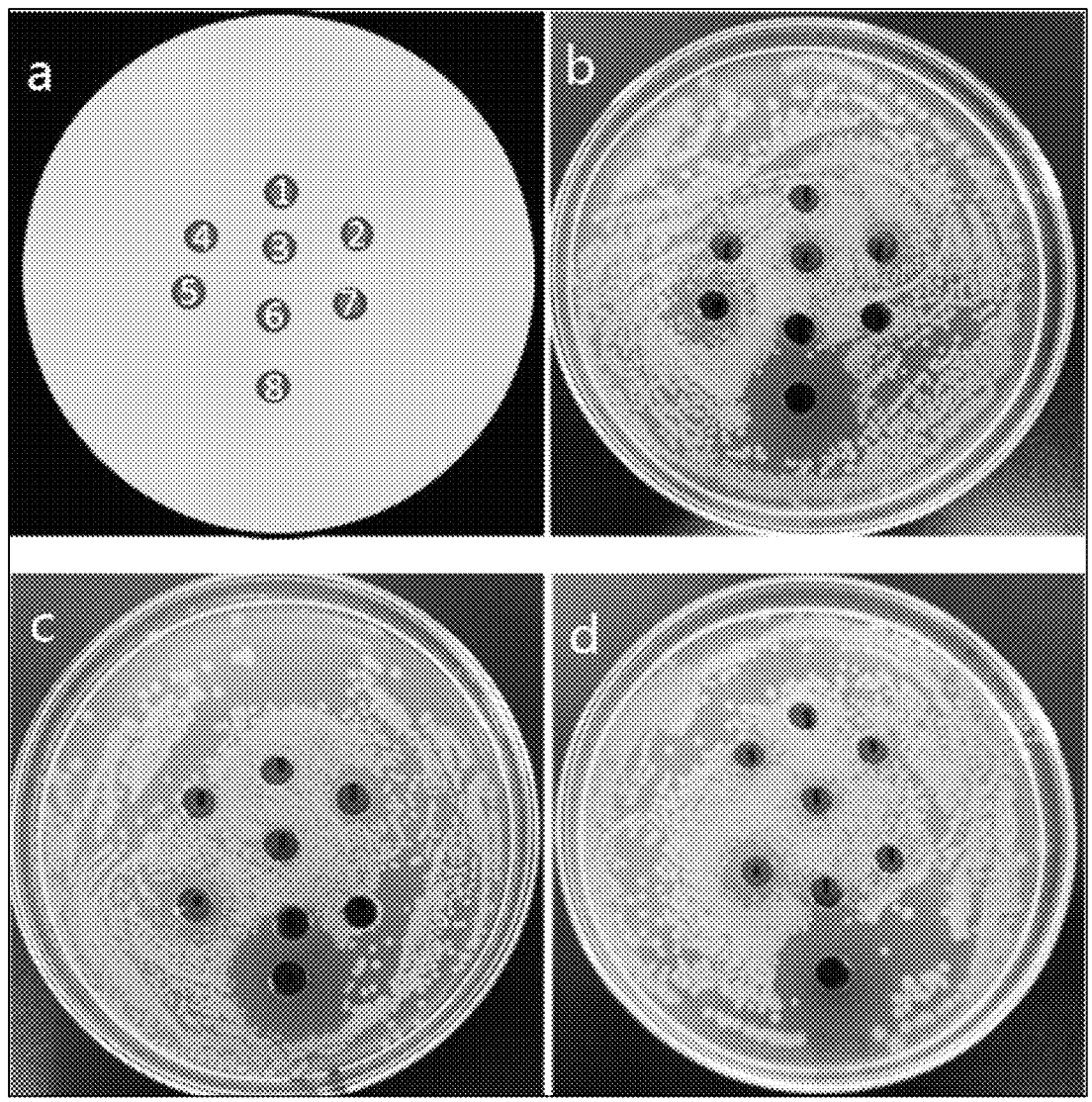
FIG. 19 shows images of bacteriostatic activity of different subjects.

Determination of antibacterial activity of polypeptides according to GB/T 39101-2020: Inhibition zone assays in the inhibition zone method evaluate the bacteriostatic activity of test substances. The strain used is *Escherichia coli* (*E. coli*) in an ampicillin solution having a concentration of 1.5 mg/mL, using the punching method instead of the "Oxford cup" method to control the sampling areas. The results are shown in FIG. 19 (repeated three times). In image a of FIG. 19, #1 represents deionized water, #2 represents AgNO$_3$, #3 represents silver nanoparticles prepared from 0.1 mol/L vitamin C for control, #4 represents a blank control, #5 represents 1.5 mg/mL ampicillin (a positive control group), #6 represents a 1 mg/mL C-β-CD/AgNPs solution, #7 represents C-β-CD, and #8 represents a 1 mg/mL thymol-encapsulated C-β-CD/AgNPs; images b-d of FIG. 19 show results of repeating the above eight samples three times.

As can be seen from FIG. 19, the thymol-encapsulated C-β-CD/AgNPs exhibited an obvious bacteriostatic effect as the diameter of the bacteriostatic circle was about 2 times that of the positive control drug; AgNO$_3$ and two types of silver nanoparticles (lyophilized after washing) exhibited a weak bacteriostatic effect; and the C-β-CD had no bacteriostatic activity.

The above descriptions are merely preferred embodiments of the present invention, and shall not be construed as limitations to the present invention. Any amendments, equivalent replacements or improvements made in the spirit and principle of the present invention shall be covered within the protection scope of the present invention.

What is claimed is:

1. A method of preparing a cationic β-cyclodextrin functionalized silver nanoparticles, comprising following steps:
    adding a cationic β-cyclodextrin to water and adjusting a pH to 10-12, then adding a silver nitrate solution and reacting at 50-70° C. to afford the cationic β-cyclodextrin functionalized silver nanoparticles;
    wherein the cationic β-cyclodextrin has a structural formula as represented below:

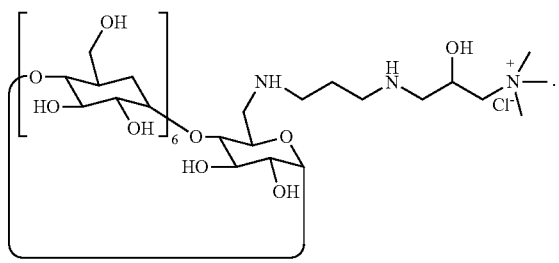

2. The method of preparing the cationic β-cyclodextrin functionalized silver nanoparticles according to claim 1, characterized in that the method for preparing the cationic β-cyclodextrin comprises following steps:
- dissolving β-cyclodextrin in an alkaline solution, and adding p-toluenesulfonyl chloride to an alkaline solution at 0-5° C., followed by stirring and reaction, to afford toluenesulfonyl-β-cyclodextrin; and
- dissolving the toluenesulfonyl-β-cyclodextrin in 1,3-propanediamine and reacting at 70-90° C. to afford diaminopropane-β-cyclodextrin; and
- dissolving 2,3-epoxypropyltrimethylammonium chloride in dimethyl sulfoxide, then adding the diaminopropane-β-cyclodextrin, and reacting at 70-90° C. to afford the cationic β-cyclodextrin.

3. The method of preparing the cationic β-cyclodextrin functionalized silver nanoparticles according to claim 2, characterized in that in the steps of preparing the toluenesulfonyl-β-cyclodextrin, a mass-volume ratio of the β-cyclodextrin, the p-toluenesulfonyl, and the alkaline solution is (45-55) g:(30-40) g:(450-550) mL; and the alkaline solution is a sodium hydroxide solution, wherein the sodium hydroxide solution has a concentration of 0.3-0.5 M.

4. The method of preparing the cationic β-cyclodextrin functionalized silver nanoparticles according to claim 2, characterized in that in the steps of preparing the diaminopropane-β-cyclodextrin, a mass-volume ratio of the toluenesulfonyl-β-cyclodextrin to the 1,3-propanediamine is (3-5) g:(15-25) mL.

5. The method of preparing the cationic β-cyclodextrin functionalized silver nanoparticles according to claim 2, characterized in that in the steps of dissolving 2,3-epoxypropyltrimethylammonium chloride in dimethyl sulfoxide and then adding the diaminopropane-β-cyclodextrin, a mass-volume ratio of the 2,3-epoxypropyltrimethylammonium chloride, the diaminopropane-β-cyclodextrin, and the dimethyl sulfoxide is (0.4-0.8) g:(4-5) g:(5-15) mL.

* * * * *